United States Patent
Denhart et al.

(10) Patent No.: US 7,105,516 B2
(45) Date of Patent: Sep. 12, 2006

(54) COMPOUNDS FOR THE TREATMENT OF PREMATURE EJACULATION

(75) Inventors: Derek John Denhart, Durham, CT (US); Jonathan L. Ditta, Middletown, CT (US); Dalton King, Hamden, CT (US); John E. Macor, Guilford, CT (US); Lawrence R. Marcin, Bethany, CT (US); Ronald J. Mattson, Meriden, CT (US); Zhaoxing Meng, Middletown, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 232 days.

(21) Appl. No.: 10/662,493

(22) Filed: Sep. 15, 2003

(65) Prior Publication Data

US 2004/0063768 A1    Apr. 1, 2004

Related U.S. Application Data

(60) Provisional application No. 60/411,663, filed on Sep. 18, 2002.

(51) Int. Cl.
 A61K 31/535  (2006.01)
 A61K 31/445  (2006.01)
 A61K 31/40   (2006.01)
 C07D 413/06  (2006.01)
 C07D 209/04  (2006.01)

(52) U.S. Cl. .................. 514/235.2; 514/323; 514/414; 544/143; 546/201; 548/455; 548/465

(58) Field of Classification Search ............... 544/143; 546/201; 548/455, 465; 514/235.2, 323
See application file for complete search history.

(56) References Cited

U.S. PATENT DOCUMENTS

| 5,468,767 | A |  | 11/1995 | Cipollina et al. |
| 5,468,768 | A |  | 11/1995 | Cipollina et al. |
| 5,583,149 | A |  | 12/1996 | Cipollina et al. |
| 5,607,961 | A |  | 3/1997  | Cipollina et al. |
| 2004/0077705 | A1 | * | 4/2004 | King et al. .......... 514/414 |

FOREIGN PATENT DOCUMENTS

WO    WO 02/079152 A1    10/2002

OTHER PUBLICATIONS

Fuller, "Pharmacologic Modification of Serotonergic Function: Drugs for the Study and Treatment of Psychiatric and Other Disorders," J. Clin. Psychiatry, 47:4 (Suppl.), Apr. 1986, pp. 4-8.

Kim, et al., "Short-Term Analysis of the Effects of As Needed Use of Sertraline at 5 p.m. for the Treatment of Premature Ejaculation," Urology, 54 (3), 1999, pp. 544-547.

McMahon, et al., "Treatment of Premature Ejaculation with Paroxetine Hydrochloride As Needed: 2 Single-Blind Placebo Controlled Crossover Studies," J. of Urology, 161, Jun. 1999, pp. 1826-1830.

Haensel, et al., "Clomipramine and Sexual Function with Men in Premature Ejaculation and Controls," J. of Urology, 156, Oct. 1996, pp. 1310-1315.

McMahon, et al., "Treatment of Premature Ejaculation with Paroxetine Hydrochloride," International Journal of Impotence Research, 11, 1999, pp. 241-246.

* cited by examiner

Primary Examiner—Johann Richter
Assistant Examiner—Ebenezer Sackey

(74) Attorney, Agent, or Firm—James Epperson; Shah R. Makujina

(57) ABSTRACT

The present invention relates to compounds of Formula (I) and pharmaceutically acceptable salts or solvates thereof and pharmaceutically acceptable formulations comprising said compounds

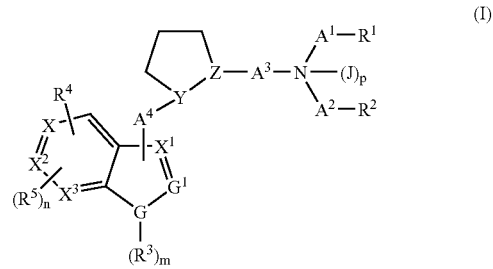

useful for the treatment of premature ejaculation, depression, attention deficit hyperactivity disorder, obsessive-compulsive disorder, post-traumatic stress disorder and substance abuse disorders.

59 Claims, No Drawings

COMPOUNDS FOR THE TREATMENT OF PREMATURE EJACULATION

CROSS REFERENCE TO RELATED APPLICATION

This non-provisional application claims priority from provisional application U.S. Ser. No. 60/411,663 filed Sep. 18, 2002.

FIELD OF THE INVENTION

The present invention relates to cyclopentylindole derivatives and pharmaceutical compositions comprising said derivatives useful for the treatment of various psychiatric disorders and premature ejaculation.

BACKGROUND OF THE INVENTION

Selective serotonin reuptake inhibitors (SSRIs) are effective for the treatment of mental depression and have been reported to be useful for treating chronic pain. See R. W. Fuller, Pharmacologic Modification of Serotonergic Function: Drugs for the Study and Treatment of Psychiatric and Other Disorders," *J. Clin. Psychiatry*, 47:4 (Suppl.) April 1986, pp. 4–8 and Selective Serotonin Reuptake Inhibitors. Edited by J P Feighner and W F Boyer, Chichester, England. John Wiley & Sons, 1991, pp 89–108. SSRI's have also demonstrated efficacy for the treatment of anxiety disorders. More recently, SSRI's have demonstrated efficacy in the treatment of premature ejaculation. See Kim and Paick, Short-term Analysis of the Effects of As Needed Use of Sertraline at 5 pm for the Treatment of Premature Ejaculation, *Urology* 54:544–547 (1999); Kim and Paick, Self Therapy with Sertraline given PRN at 5 pm in treatment of Premature Ejaculation, *Journal of Urology* 54:544–547 (1998); McMahon and Touma, Treatment of Premature Ejaculation with Paroxetine Hydrochloride As Needed: 2 Single-Blind Placebo Controlled Crossover Studies *Journal of Urology* 161:1826–1830 (1999); Haensal et al., Clomipramine and sexual function in men with premature ejaculation and controls *Journal of Urology* 158:1310–1315 (1998); and McMahon and Touma, Treatment of Premature Ejaculation with Paraoxetine Hydrochloride *International Journal Impotence Research* 11:241–246 (1999).

In U.S. Pat. No. 5,468,768, $C_{5-7}$cycloalkyl indole derivatives, more particularly examples of substituted indol-3-yl cyclohexyl amines were disclosed for the treatment of headache. See also U.S. Pat. No. 5,583,149. In U.S. Pat. No. 5,468,767 $C_{5-7}$cycloalkyl indole derivatives, more particularly examples of substituted indol-3-yl cyclohexyl amines were disclosed for the treatment of depression. See also U.S. Pat. No. 5,607,961. None of said patents discloses use of said derivatives for the treatment of premature ejaculation. Moreover, none of said patents generically or specifically disclose 1,2-cyclopentyl substitutions. Thus, novel SSRI's effective for the treatment of premature ejaculation and other disorders would be greatly advantageous.

SUMMARY OF THE INVENTION

Thus according to a first embodiment of a first aspect of the present invention are provided compounds of Formula (I)

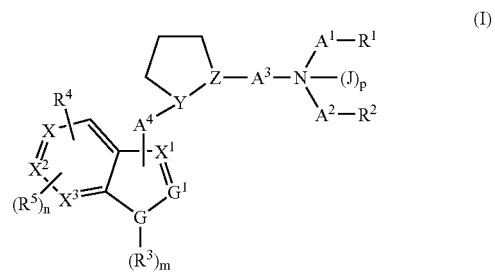

and pharmaceutically acceptable salts or solvates thereof wherein $A^1$ and $A^2$ are each independently $C_{1-4}$alkylene or a bond;

$A^3$ is a bond, $C_{1-4}$alkylene or $C_{1-4}$alkylidene;

$A^4$ is $C_{1-4}$alkylene or a bond and is attached to X, $X^1$ or $X^2$;

X, $X^1$, $X^2$ and $X^3$ are independently C or CH;

J is $C_{1-4}$alkyl;

p is 0 or 1;

$R^1$ and $R^2$ are independently H, $C_{1-3}$alkyl, $C_{3-6}$cycloalkyl, phenyl, —O-phenyl, —N(H)C(O)O—$C_{1-4}$alkyl or $C_{1-4}$alkyl-N(H)C(O)O—;

said $C_{3-6}$cycloalkyl, phenyl or O-phenyl being independently and optionally substituted with $C_{1-4}$alkyl, $C_{1-3}$alkoxy, indolyl or halo;

wherein said indolyl is optionally substituted by halo or cyano;

or are independently selected from the group of heterocyclic moieties consisting of thienyl, furanyl, pyrrolyl, pyrrolinyl, pyrrolidinyl, imidazolyl, imidazolinyl, imidazolidinyl, pyrazolyl, pyrazolinyl, pyrazolidinyl, pyridyl, pyrimidinyl, piperidinyl, piperazinyl, morpholino, adamantyl, indolyl, isoindolyl, indolinyl, quinolinyl, dihydroquinolinyl, tetrahydroquinolinyl, isoquinolinyl, dihydroisoquinolinyl and tetrahydroisoquinolinyl, wherein said heterocyclic moieties are optionally substituted with halo, $C_{1-4}$alkyl, $C_{1-4}$alkoxy or cyano;

or wherein -$A^1$-$R^1$ and -$A^2$-$R^2$ together with the nitrogen to which they are attached form pyrrolyl, pyrrolinyl, pyrrolidinyl, imidazolyl, imidazolinyl, imidazolidinyl, pyrazolyl, pyrazolinyl, pyrazolidinyl, pyridyl, pyrimidinyl, piperidinyl, piperazinyl, morpholino, indolyl, isoindolyl, indolinyl, isoindolinyl, quinolinyl, dihydroquinolinyl, tetrahydroquinolinyl, isoquinolinyl, dihydroisoquinolinyl or tetrahydroisoquinolinyl and are optionally substituted with halo, $C_{1-4}$alkyl, $C_{1-4}$alkoxy, cyano or benzyl;

$R^3$ is H or $C_{1-4}$alkyl;

m is 0 or 1;

$R^4$ and $R^5$ are independently hydrogen, cyano, halo, nitro, $C_{1-3}$alkyl or $C_{1-3}$perfluoroalkyl;

wherein said $R^4$ or $R^5$ may be independently attached to $G^1$, X, $X^1$, $X^2$ or $X^3$;

n is 0 or 1;

G is N, O or S;

$G^1$ is N, C or CH;

Y is (D)H wherein D is C; and

Z is (E)H wherein E is C;

provided that
both $R^4$ and $R^5$ are not attached to the same of said $G^1$, X, $X^1$, $X^2$ or $X^3$;
if G O is or S, then m is 0;
if G is N, then m is 1;
if $R_1$ is $C_{3-6}$cycloalkyl, phenyl or O-phenyl being independently and optionally substituted with $C_{1-4}$alkyl, $C_{1-3}$alkoxy, indolyl or halo; wherein said indolyl is optionally substituted by halo or cyano, then $R_2$ is H or $C_{1-3}$alkyl;
if $R_2$ is $C_{3-6}$cycloalkyl, phenyl or O-phenyl being independently and optionally substituted with $C_{1-4}$alkyl, $C_{1-3}$alkoxy, indolyl or halo; wherein said indolyl is optionally substituted by halo or cyano, then $R^1$ is H or $C_{1-3}$alkyl;
if -$A^1$-$R^1$ and -$A^2$-$R^2$ together with the nitrogen to which they are attached form pyrrolyl, pyrrolinyl, pyrrolidinyl, imidazolyl, imidazolinyl, imidazolidinyl, pyrazolyl, pyrazolinyl, pyrazolidinyl, pyridyl, pyrimidinyl, piperidinyl, piperazinyl, morpholino, indolyl, isoindolyl, indolinyl, isoindolinyl, quinolinyl, dihydroquinolinyl, tetrahydroquinolinyl, isoquinolinyl, dihydroisoquinolinyl or tetrahydroisoquinolinyl and are optionally substituted with halo, $C_{1-4}$alkyl, $C_{1-4}$alkoxy, cyano or benzyl, then p is 0;
if $R^1$ is —N(H)C(O)O$C_{1-4}$alkyl, $C_{1-4}$alkyl-N(H)C(O)O— or said heterocyclic moiety wherein said heterocyclic moiety contains a nitrogen atom and said nitrogen atom is attached to $A^1$, then $A^1$ is $C_{2-4}$alkylene;
if $R^2$ is —N(H)C(O)O$C_{1-4}$alkyl, $C_{1-4}$alkyl-N(H)C(O)O— or said heterocyclic moiety wherein said heterocyclic moiety contains a nitrogen atom and said nitrogen atom is attached to $A^2$, then $A^2$ is $C_{2-4}$alkylene;
if $R^1$ is N(H)C(O)O—$C_{1-4}$alkyl, $C_{1-4}$alkyl-N(H)C(O)O— or a heterocyclic moiety selected from the group consisting of thienyl, furanyl, pyrrolyl, pyrrolinyl, pyrrolidinyl, imidazolyl, imidazolinyl, imidazolidinyl, pyrazolyl, pyrazolinyl, pyrazolidinyl, pyridyl, pyrimidinyl, piperidinyl, piperazinyl, morpholino, adamantyl, indolyl, isoindolyl, indolinyl, quinolinyl, dihydroquinolinyl, tetrahydroquinolinyl, isoquinolinyl, dihydroisoquinolinyl and tetrahydroisoquinolinyl, wherein said heterocyclic moieties are optionally substituted with halo, $C_{1-4}$alkyl, $C_{1-4}$alkoxy or cyano, then $R^2$ is H or $C_{1-3}$alkyl;
if $R^2$ is —N(H)C(O)O—$C_{1-4}$alkyl, $C_{1-4}$alkyl-N(H)C(O)O— or a heterocyclic moiety selected from the group consisting of thienyl, furanyl, pyrrolyl, pyrrolinyl, pyrrolidinyl, imidazolyl, imidazolinyl, imidazolidinyl, pyrazolyl, pyrazolinyl, pyrazolidinyl, pyridyl, pyrimidinyl, piperidinyl, piperazinyl, morpholino, adamantyl, indolyl, isoindolyl, indolinyl, quinolinyl, dihydroquinolinyl, tetrahydroquinolinyl, isoquinolinyl, dihydroisoquinolinyl and tetrahydroisoquinolinyl, wherein said heterocyclic moieties are optionally substituted with halo, $C_{1-4}$alkyl, $C_{1-4}$alkoxy or cyano, then $R^1$ is H or $C_{1-3}$alkyl;
if $R^4$ or $R^5$ are attached to $G^1$, then $G^1$ is C;
if $A^4$, $R^4$ or $R^5$ are attached to X, then X is C;
if $A^4$, $R^4$ or $R^5$ are attached to $X^1$, then $X^1$ is C;
if $A^4$, $R^4$ or $R^5$ are attached to $X^2$, then $X^2$ is C;
if $R^4$ or $R^5$ are attached to $X^3$, then $X^3$ is C.

According to another embodiment of the first aspect of the present invention are provided compounds of Formula (I) according to the first embodiment of the first aspect wherein p is 0.

According to another embodiment of the first aspect of the present invention are provided compounds of Formula (I) according to the first embodiment of the first aspect wherein G is N and $G^1$ is CH.

According to another embodiment of the first aspect of the present invention are provided compounds of Formula (I) according to the first embodiment of the first aspect wherein G is S and $G^1$ is CH.

According to another embodiment of the first aspect of the present invention are provided compounds of Formula (I) according to the first embodiment of the first aspect wherein G is N and $G^1$ is N.

According to another embodiment of the first aspect of the present invention are provided compounds of Formula (I) according to the first embodiment of the first aspect wherein G is S and $G^1$ is N.

According to another embodiment of the first aspect of the present invention are provided compounds of Formula (I) according to the first embodiment of the first aspect wherein G is O and $G^1$ is N.

According to another embodiment of the first aspect of the present invention are provided compounds of Formula (I) according to the first embodiment of the first aspect wherein $R^1$ is methyl and $R^2$ is methyl.

According to another embodiment of the first aspect of the present invention are provided compounds of Formula (I) according to the first embodiment of the first aspect wherein $R^1$ is H and $R^2$ is $C_{3-6}$cycloalkyl wherein said $C_{3-6}$cycloalkyl is substituted with indolyl and wherein said indolyl is optionally substituted by halo or cyano.

According to another embodiment of the first aspect of the present invention are provided compounds of Formula (I) according to the first embodiment of the first aspect wherein $A^1$ is a bond, $R^1$ is methyl, $A^2$ is a bond and $R^2$ is methyl.

According to another embodiment of the first aspect of the present invention are provided compounds of Formula (I) according to the first embodiment of the first aspect wherein $R^3$ is H and m is 1.

According to another embodiment of the first aspect of the present invention are provided compounds of Formula (I) according to the first embodiment of the first aspect wherein $R^3$ is methyl and m is 1.

According to another embodiment of the first aspect of the present invention are provided compounds of Formula (I) according to the first embodiment of the first aspect wherein $R^4$ and $R^5$ are halo.

According to another embodiment of the first aspect of the present invention are provided compounds of Formula (I) according to the first embodiment of the first aspect wherein $R^4$ is $C_{1-3}$alkyl and is attached to $G^1$.

According to another embodiment of the first aspect of the present invention are provided compounds of Formula (I) according to the first embodiment of the first aspect wherein $R^4$ is $C_{1-3}$perfluoroalkyl and is attached to $G^1$.

According to another embodiment of the first aspect of the present invention are provided compounds of Formula (I) according to the first embodiment of the first aspect wherein $R^4$ is hydrogen.

According to another embodiment of the first aspect of the present invention are provided compounds of Formula (I) according to the first embodiment of the first aspect wherein $R^4$ is fluoro.

According to another embodiment of the first aspect of the present invention are provided compounds of Formula (I) according to the first embodiment of the first aspect wherein $R^4$ is cyano.

According to another embodiment of the first aspect of the present invention are provided compounds of Formula (I) according to the first embodiment of the first aspect wherein $R^4$ and $R^5$ are each fluoro.

According to another embodiment of the first aspect of the present invention are compounds of Formula (I) wherein the hydrogen atom attached to D is in the trans configuration to the hydrogen atom attached to E.

According to another embodiment of the first aspect of the present invention are compounds of Formula (I) wherein the hydrogen atom attached to D is in the cis configuration to the hydrogen atom attached to E.

According to another embodiment of the first aspect of the present invention are compounds of Formula (I) wherein D in relation to the four moieties to which it is attached has an absolute configuration of S; E in relation to the four moieties to which it is attached has an absolute configuration of S.

According to another embodiment of the first aspect of the present invention are compounds of Formula (I) wherein D in relation to the four moieties to which it is attached has an absolute configuration of S; E in relation to the four moieties to which it is attached has an absolute configuration of R.

According to another embodiment of the first aspect of the present invention are compounds of Formula (I) wherein D in relation to the four moieties to which it is attached has an absolute configuration of R; E in relation to the four moieties to which it is attached has an absolute configuration of S.

According to another embodiment of the first aspect of the present invention are compounds of Formula (I) wherein D in relation to the four moieties to which it is attached has an absolute configuration of R; E in relation to the four moieties to which it is attached has an absolute configuration of R.

According to another embodiment of the first aspect of the present invention are provided compounds of Formula (I) according to the first embodiment of the first aspect wherein $A^3$ is $C_{1-4}$alkylene.

According to another embodiment of the first aspect of the present invention are provided compounds of Formula (I) according to the first embodiment of the first aspect wherein $A^3$ is $C_{1-4}$alkylidene.

According to another embodiment of the first aspect of the present invention are provided compounds of Formula (I) according to the first embodiment of the first aspect wherein $A^3$ is methylene.

According to another embodiment of the first aspect of the present invention are provided compounds of Formula (I) according to the first embodiment of the first aspect wherein $A^3$ is a bond.

According to another embodiment of the first aspect of the present invention are provided compounds of Formula (I) according to the first embodiment of the first aspect wherein $A^4$ is a bond.

According to another embodiment of the first aspect of the present invention are provided compounds of Formula (I) according to the first embodiment of the first aspect wherein $A^4$ is methylene.

According to another embodiment of the first aspect of the present invention are provided compounds of Formula (I) according to the first embodiment of the first aspect wherein $A^4$ is attached $X^1$.

According to another embodiment of the first aspect of the present invention are provided compounds of Formula (I) according to the first embodiment of the first aspect wherein $A^4$ is attached X.

According to another embodiment of the first aspect of the present invention are provided compounds of Formula (I) according to the first embodiment of the first aspect wherein $R^4$ is attached X.

According to another embodiment of the first aspect of the present invention are provided compounds of Formula (I) according to the first embodiment of the first aspect wherein $R^4$ is attached $X^1$.

According to another embodiment of the first aspect of the present invention are provided compounds of Formula (I) according to the first embodiment of the first aspect wherein $R^4$ is cyano or halo and n is 0.

According to another embodiment of the first aspect of the present invention are provided compounds of Formula (I) according to the first embodiment of the first aspect wherein $R^1$ is independently selected from the group of heterocyclic moieties consisting of thienyl, furanyl, pyrrolyl, pyrrolinyl, pyrrolidinyl, imidazolyl, imidazolinyl, imidazolidinyl, pyrazolyl, pyrazolinyl, pyrazolidinyl, pyridyl, pyrimidinyl, piperidinyl, piperazinyl, morpholino, adamantyl, indolyl, isoindolyl, indolinyl, quinolinyl, dihydroquinolinyl, tetrahydroquinolinyl, isoquinolinyl, dihydroisoquinolinyl and tetrahydroisoquinolinyl, wherein said heterocyclic moieties are optionally substituted with halo, $C_{1-4}$alkyl, $C_{1-4}$alkoxy or cyano; $A^1$ is $C_{1-4}$alkylene; $R^2$ is H or $C_{1-3}$alkylene; and $A^2$ is a bond.

According to another embodiment of the first aspect of the present invention are provided compounds of Formula (I) according to the first embodiment of the first aspect wherein $R^1$ is independently selected from the group of heterocyclic moieties consisting of thienyl, imidazolyl, pyridyl, piperidinyl, piperazinyl, morpholino, adamantyl, indolyl, tetrahydroquinolinyl and tetrahydroisoquinolinyl; $A^1$ is $C_{1-4}$alkylene; $R^2$ is H or $C_{1-3}$alkylene; and $A^2$ is a bond.

According to another embodiment of the first aspect of the present invention are provided compounds of Formula (I) according to the first embodiment of the first aspect wherein $R^2$ is independently selected from the group of heterocyclic moieties consisting of thienyl, furanyl, pyrrolyl, pyrrolinyl, pyrrolidinyl, imidazolyl, imidazolinyl, imidazolidinyl, pyrazolyl, pyrazolinyl, pyrazolidinyl, pyridyl, pyrimidinyl, piperidinyl, piperazinyl, morpholino, adamantyl, indolyl, isoindolyl, indolinyl, quinolinyl, dihydroquinolinyl, tetrahydroquinolinyl, isoquinolinyl, dihydroisoquinolinyl and tetrahydroisoquinolinyl, wherein said heterocyclic moieties are optionally substituted with halo, $C_{1-4}$alkyl, $C_{1-4}$alkoxy or cyano; $A^2$ is $C_{1-4}$alkylene; $R^1$ is H or $C_{1-3}$alkylene; and $A^1$ is a bond.

According to another embodiment of the first aspect of the present invention are provided compounds of Formula (I) according to the first embodiment of the first aspect wherein $R^2$ is independently selected from the group of heterocyclic moieties consisting of thienyl, imidazolyl, pyridyl, piperidinyl, piperazinyl, morpholino, adamantyl, indolyl, tetrahydroquinolinyl and tetrahydroisoquinolinyl; $A^2$ is $C_{1-4}$alkylene; $R^1$ is H or $C_{1-3}$alkylene; and $A^1$ is a bond.

According to another embodiment of the first aspect of the present invention are provided compounds of Formula (I) according to the first embodiment of the first aspect wherein $R^1$ and $R^2$ are independently H, $C_{1-3}$alkyl, $C_{3-6}$cycloalkyl, phenyl, —O-phenyl, or —N(H)C(O)O—$C_{1-4}$alkyl.

According to another embodiment of the first aspect of the present invention are provided compounds of Formula (I)

according to the first embodiment of the first aspect wherein $R^1$ and $R^2$ are independently H, $C_{1-3}$alkyl, or —N(H)C(O)O—$C_{1-4}$alkyl. According to another embodiment of the first aspect of the present invention are provided compounds of Formula (I) according to the first embodiment of the first aspect wherein $R^1$ and $R^2$ are independently H, $C_{1-3}$alkyl, $C_{3-6}$cycloalkyl, phenyl, or —O-phenyl.

According to another embodiment of the first aspect of the present invention are provided compounds of Formula (I) according to the first embodiment of the first aspect wherein $R^1$ and $R^2$ are independently H, $C_{1-3}$alkyl, or are independently selected from the group of heterocyclic moieties consisting of thienyl, imidazolyl, pyridyl, piperidinyl, piperazinyl, morpholino, adamantyl, indolyl, tetrahydroquinolinyl and tetrahydroisoquinolinyl.

According to another embodiment of the first aspect of the present invention are provided compounds of Formula (I) according to the first embodiment of the first aspect wherein $R^2$ is H or $C_{1-3}$alkyl and $R^1$ is $C_{3-6}$cycloalkyl, phenyl, —O-phenyl, or —N(H)C(O)O—$C_{1-4}$alkyl.

According to another embodiment of the first aspect of the present invention are provided compounds of Formula (I) according to the first embodiment of the first aspect wherein $R^2$ is H or $C_{1-3}$alkyl and $R^1$ is N(H)C(O)O—$C_{1-4}$alkyl.

According to another embodiment of the first aspect of the present invention are provided compounds of Formula (I) according to the first embodiment of the first aspect wherein $R^2$ is H or $C_{1-3}$alkyl and $R^1$ is $C_{3-6}$cycloalkyl, phenyl or —O-phenyl.

According to another embodiment of the first aspect of the present invention are provided compounds of Formula (I) according to the first embodiment of the first aspect wherein $R^2$ is H or $C_{1-3}$alkyl and $R^1$ is selected from the group of heterocyclic moieties consisting of thienyl, imidazolyl, pyridyl, piperidinyl, piperazinyl, morpholino, adamantyl, indolyl, tetrahydroquinolinyl and tetrahydroisoquinolinyl.

According to another embodiment of the first aspect of the present invention are provided compounds of Formula (I) according to the first embodiment of the first aspect wherein $R^1$ is H or $C_{1-3}$alkyl and $R^2$ is $C_{3-6}$cycloalkyl, phenyl, —O-phenyl, or —N(H)C(O)O—$C_{1-4}$alkyl.

According to another embodiment of the first aspect of the present invention are provided compounds of Formula (I) according to the first embodiment of the first aspect wherein $R^1$ is H or $C_{1-3}$alkyl and $R^2$ is N(H)C(O)O—$C_{1-4}$alkyl.

According to another embodiment of the first aspect of the present invention are provided compounds of Formula (I) according to the first embodiment of the first aspect wherein $R^1$ is H or $C_{1-3}$alkyl and $R^2$ is $C_{3-6}$cycloalkyl, phenyl or —O-phenyl.

According to another embodiment of the first aspect of the present invention are provided compounds of Formula (I) according to the first embodiment of the first aspect wherein $R^1$ is H or $C_{1-3}$alkyl and $R^2$ is selected from the group of heterocyclic moieties consisting of thienyl, imidazolyl, pyridyl, piperidinyl, piperazinyl, morpholino, adamantyl, indolyl, tetrahydroquinolinyl and tetrahydroisoquinolinyl.

According to another embodiment of the first aspect of the present invention are provided compounds of Formula (I) according to the first embodiment of the first aspect wherein -$A^1$-$R^1$ and -$A^2$-$R^2$ together with the nitrogen to which they are attached form pyrrolidinyl, piperidinyl, piperazinyl, morpholino, tetrahydroquinolinyl or tetrahydroisoquinolinyl and are optionally substituted with benzyl.

According to another embodiment of the first aspect of the present invention are provided compounds of Formula (I) according to the first embodiment of the first aspect wherein $A^1$ and $A^2$ are each independently $C_{1-4}$alkylene or a bond;
$A^3$ is $C_{1-4}$alkylene;
$A^4$ is bond and is attached to X or $X^1$;
X and $X^1$ are each independently C or CH;
$X^2$ and $X^3$ are each CH;
p is 0;
$R^1$ and $R^2$ are independently H, $C_{1-3}$alkyl, $C_{3-6}$cycloalkyl, phenyl, —O-phenyl, —N(H)C(O)O—$C_{1-4}$alkyl or $C_{1-4}$alkyl-N(H)C(O)O—;
said $C_{3-6}$cycloalkyl, phenyl or O-phenyl being independently and optionally substituted with $C_{1-4}$alkyl, $C_{1-3}$alkoxy or halo;
or are independently selected from the group of heterocyclic moieties consisting of thienyl, furanyl, pyrrolyl, pyrrolinyl, pyrrolidinyl, imidazolyl, imidazolinyl, imidazolidinyl, pyrazolyl, pyrazolinyl, pyrazolidinyl, pyridyl, pyrimidinyl, piperidinyl, piperazinyl, morpholino, adamantyl, indolyl, isoindolyl, indolinyl, quinolinyl, dihydroquinolinyl, tetrahydroquinolinyl, isoquinolinyl, dihydroisoquinolinyl and tetrahydroisoquinolinyl, wherein said heterocyclic moieties are optionally substituted with halo, $C_{1-4}$alkyl, $C_4$alkoxy or cyano;
or wherein -$A^1$-$R^1$ and -$A^2$-$R^2$ together with the nitrogen to which they are attached form pyrrolyl, pyrrolinyl, pyrrolidinyl, imidazolyl, imidazolinyl, imidazolidinyl, pyrazolyl, pyrazolinyl, pyrazolidinyl, pyridyl, pyrimidinyl, piperidinyl, piperazinyl, morpholino, indolyl, isoindolyl, indolinyl, isoindolinyl, quinolinyl, dihydroquinolinyl, tetrahydroquinolinyl, isoquinolinyl, dihydroisoquinolinyl or tetrahydroisoquinolinyl and are optionally substituted with halo, $C_{1-4}$alkyl, $C_{1-4}$alkoxy, cyano or benzyl;
$R^3$ is H or $C_{1-4}$alkyl;
m is 1;
$R^4$ is hydrogen, cyano, halo, nitro, $C_{1-3}$alkyl or $C_{1-3}$perfluoroalkyl and is attached to X or $X^1$;
n is 0;
G is N;
$G^1$ is CH;
Y is (D)H wherein D is C; and
Z is (E)H wherein E is C;
provided that
if $R^1$ is —N(H)C(O)O$C_{1-4}$alkyl, $C_{1-4}$alkyl-N(H)C(O)O— or said heterocyclic moiety wherein said heterocyclic moiety contains a nitrogen atom and said nitrogen atom is attached to $A^1$, then $A^1$ is $C_{2-4}$alkylene;
if $R^2$ is —N(H)C(O)O$C_{1-4}$alkyl, $C_{1-4}$alkyl-N(H)C(O)O— or said heterocyclic moiety wherein said heterocyclic moiety contains a nitrogen atom and said nitrogen atom is attached to $A^2$, then $A^2$ is $C_{2-4}$alkylene;
if $R^1$ is N(H)C(O)O—$C_{1-4}$alkyl, $C_{1-4}$alkyl-N(H)C(O)O— or a heterocyclic moiety selected from the group consisting of thienyl, furanyl, pyrrolyl, pyrrolinyl, pyrrolidinyl, imidazolyl, imidazolinyl, imidazolidinyl, pyrazolyl, pyrazolinyl, pyrazolidinyl, pyridyl, pyrimidinyl, piperidinyl, piperazinyl, morpholino, adamantyl, indolyl, isoindolyl, indolinyl, quinolinyl, dihydroquinolinyl, tetrahydroquinolinyl, isoquinolinyl, dihydroisoquinolinyl and tetrahydroisoquinolinyl, wherein said heterocyclic moieties are optionally substituted with halo, $C_{1-4}$alkyl, $C_{1-4}$alkoxy or cyano, then $R^2$ is H or $C_{1-3}$alkyl;
if $R^2$ is —N(H)C(O)O—$C_{1-4}$alkyl, $C_{1-4}$alkyl-N(H)C(O)O— or a heterocyclic moiety selected from the group consisting of thienyl, furanyl, pyrrolyl, pyrrolinyl, pyrrolidinyl, imidazolyl, imidazolinyl, imidazolidinyl, pyrazolyl, pyrazolinyl, pyrazolidinyl, pyridyl, pyrimidinyl, piperidinyl, piperazinyl, morpholino, adamantyl, indolyl, isoindolyl, indolinyl, quinolinyl, dihydroquinolinyl, tetrahydroquinolinyl, isoquinolinyl, dihydroisoquinolinyl and tetrahydroisoquinolinyl, wherein said heterocyclic moieties are optionally substituted with halo, $C_{1-4}$alkyl, $C_{1-4}$alkoxy or cyano, then $R^1$ is H or $C_{1-3}$alkyl;

if $A^4$ or $R^4$ are attached to X, then X is C;

if $A^4$ or $R^4$ are attached to $X^1$, then $X^1$ is C.

According to various embodiments of a second aspect of the present invention are provided pharmaceutically acceptable formulations comprising compounds of Formula (I) as defined herein.

Disorders of particular interest include depression, attention deficit hyperactivity disorder, obsessive-compulsive disorder, post-traumatic stress disorder, substance abuse disorders and sexual dysfunction including (in particular) premature ejaculation. The compounds of the present invention may be administered alone or as part of a combination therapy.

Premature ejaculation may be defined as persistent or recurrent ejaculation before, upon or shortly after penile penetration of a sexual partner. It may also be defined as ejaculation occurring before the individual wishes [see *The Merck Manual*, 16$^{th}$ edition, p. 1576, published by Merck Research Laboratories, 1992]. Thus according to various embodiments of a third aspect of the present invention are provided methods of treating conditions selected from the group consisting of depression, attention deficit hyperactivity disorder, obsessive-compulsive disorder, post-traumatic stress disorder, substance abuse disorders and sexual dysfunction including and in particular premature ejaculation comprising the administration to a human in need thereof an effective amount of pharmaceutically acceptable formulations comprising compounds of the present invention as defined herein.

Other embodiments of the present invention may comprise suitable combinations of two or more of the embodiments and/or aspects disclosed herein.

Yet other embodiments and aspects of the invention will be apparent according to the description provided below.

DETAILED DESCRIPTION OF THE INVENTION

The description of the invention herein should be construed in congruity with the laws and principals of chemical bonding. For example, it may be necessary to remove a hydrogen atom in order accommodate a substituent at any given location.

An embodiment or aspect which depends from another embodiment or aspect, will describe only the variables having values or provisos that differ from the embodiment or aspect from which it depends.

If a variable is quantified with a value of zero, then any bond attaching said variable should no longer be represented, e.g., if n in ($R^3$), equals 0, then the bond attaching $R^3$ to G should no longer be represented.

As used herein, "halo" or "halogen" includes fluoro, chloro, bromo and iodo.

As used herein, "$C_{1-4}$alkylene" means a one to four carbon alkane having one hydrogen atom removed from two different carbon atoms in said alkane, e.g., —$CH_2CH_2CH_2$—.

As used herein, "$C_{1-4}$alkylidene" means a one to four carbon alkane having two hydrogen atoms removed from one carbon atom in said alkane, e.g.,

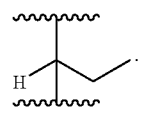

As used in the embodiments and claims herein the term "bond" is used as a means of eliminating an intervening variable to allow for a direct link between the remaining variables or atoms. For example, if where "$A^1$ and $A^2$ are each independently $C_{1-4}$alkylene or a bond" $A^1$ is a bond, then $R^1$ is attached to N via a single bond.

It should be understood that the alternating double bond designations in the six-membered ring of the 5,6-membered fused structure represented in Formula (I) are relative and represent the delocalized π orbital electrons of said ring.

It is to be understood that the present invention may include any and all possible stereoisomers, geometric isomers, diastereoisomers, enantiomers, anomers and optical isomers, unless a particular description specifies otherwise.

The compounds of this invention may exist in the form of pharmaceutically acceptable salts. Such salts may include addition salts with inorganic acids such as, for example, hydrochloric acid and sulfuric acid, and with organic acids such as, for example, acetic acid, citric acid, methanesulfonic acid, toluenesulfonic acid, tartaric acid and maleic acid. Further, in case the compounds of this invention contain an acidic group, the acidic group may exist in the form of alkali metal salts such as, for example, a potassium salt and a sodium salt; alkaline earth metal salts such as, for example, a magnesium salt and a calcium salt; and salts with organic bases such as a triethylammonium salt and an arginine salt. In the case of a sublingual formulation a saccharin salt or maleate salt may be of particular benefit. The compounds of the present invention may be hydrated or non-hydrated.

The compounds of this invention can be administered in such oral dosage forms as tablets, capsules (each of which includes sustained release or timed release formulations), pills, powders, granules, elixirs, tinctures, suspensions, syrups and emulsions. The compounds of this invention may also be administered intravenously, intraperitoneally, subcutaneously, or intramuscularly, all using dosage forms well known to those skilled in the pharmaceutical arts. The compounds can be administered alone, but generally will be administered with a pharmaceutical carrier selected upon the basis of the chosen route of administration and standard pharmaceutical practice. Compounds of this invention can also be administered in intranasal form by topical use of suitable intranasal vehicles, or by transdermal routes, using transdermal skin patches. When compounds of this invention are administered transdermally the dosage will be continuous throughout the dosage regimen.

The dosage and dosage regimen and scheduling of a compounds of the present invention must in each case be carefully adjusted, utilizing sound professional judgment and considering the age, weight and condition of the recipient, the route of administration and the nature and extent of the disease condition. In accordance with good clinical practice, it is preferred to administer the instant compounds at a concentration level which will produce effective beneficial effects without causing any harmful or untoward side effects.

Synthesis

Compounds of the present invention may be synthesized according to the general schema provided below. Variables provided in the schema below are defined in accordance with the description of compounds of the above Formulae unless otherwise specified.

A preferred method for the preparation of trans-substituted compounds of Formula I is illustrated in Scheme 1. Appropriately substituted indoles 1 are condensed in the presence of condensation catalysts with an appropriately substituted cyclic aldehydes give the trans-1,2-disubstituted intermediates, 2. Subsequent reductive amination of 2 using an appropriately substituted amine in the presence of sodium cyanoborohydride, sodium triacetoxyborohydride, or the like, provides, after the removal of any protecting groups, the compounds of Formula I.

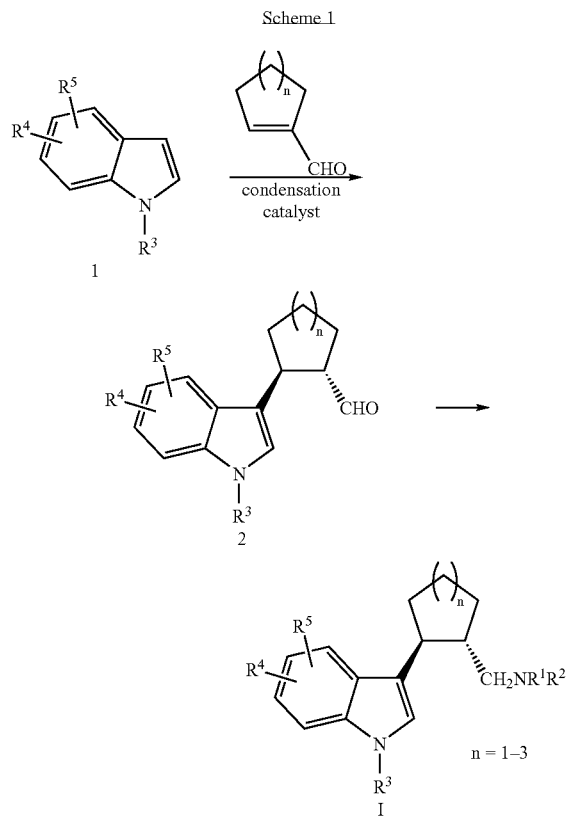

Racemic condensation catalysts can be used in the process described in Scheme 1 to provide racemic intermediates 2, and subsequently racemic compounds of Formula I. One skilled in the art can appreciate that single enantiomers of chiral compounds can have different activities, making one enantiomer more preferred than the other. The separation of the single enantiomers of the compounds of Formula I can be done by classical resolution methods, such as recrystallization of the salts of the amine with chiral acids such as camphor sulfonic acid, tartaric acid, or the like. Alternatively, the single enantiomers can be separated by chromatography on a chiral HPLC column. In the route of Scheme 1, one skilled in the art can also appreciate that chiral condensation catalysts [such as those described in: Journal of the American Chemical Society (2002), 124(11), 2458–2460; and PCT Int. Appl. (2003), WO 0347740 A2 20030612; and the like] can be used to provide intermediates 2 stereoselectively, and subsequently single enantiomers of compounds of Formula I.

Another method for the preparation of trans-substituted compounds of Formula I is illustrated in Scheme 2. An appropriately substituted, metallated indole 3, where M is a group such as $B(OH)_2$, $Sn(n-Bu)_3$, magnesium, lithium, or the like, is condensed in the presence of an appropriate catalyst with an appropriately substituted cycloalkenyl carboxylic acid ester, amide, ketone, or the like to give intermediate 4. Subsequent reduction of 4 using reagents such as hydrogen over palladium catalysts, or the like, provides the cis-disubstituted intermediate 5. This material is hydrolyzed and equilibrated to the trans-substituted carboxylic acid 6 using reagents such as lithium hydroxide in solvents such as methanol and water. Acid 6 is then converted to the corresponding carboxaldehyde 7 by methods known to those skilled in the art. One such method involves conversion the acid to the N-methoxy-N-methyl amide, with subsequent reduction using reducing agents such as lithium aluminum hydride to give carboxaldehyde 7. The carboxaldehyde 7 is then reductively aminated with an appropriate amine using reducing reagents such as sodium cyanoborohydride, sodium triacetoxyborohydride, or the like, to give, after the removal of any protecting groups, the compound of Formula I.

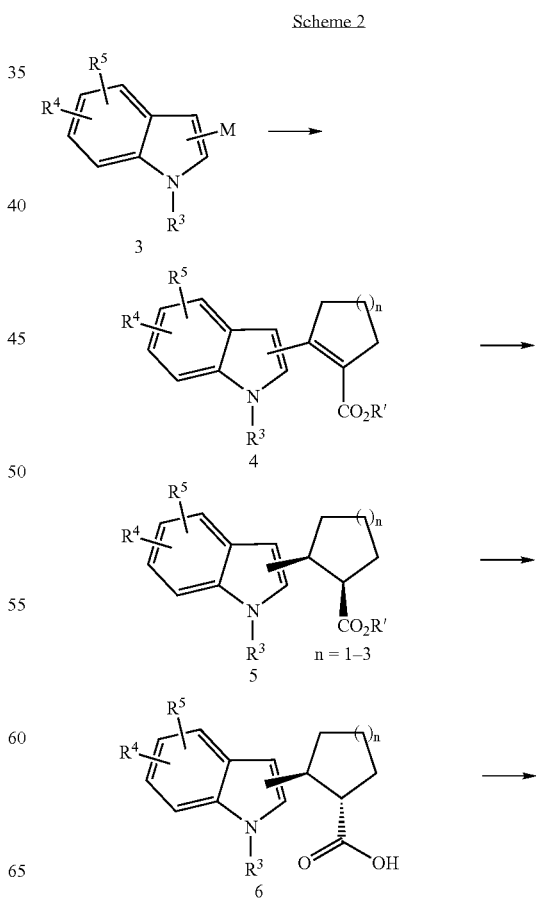

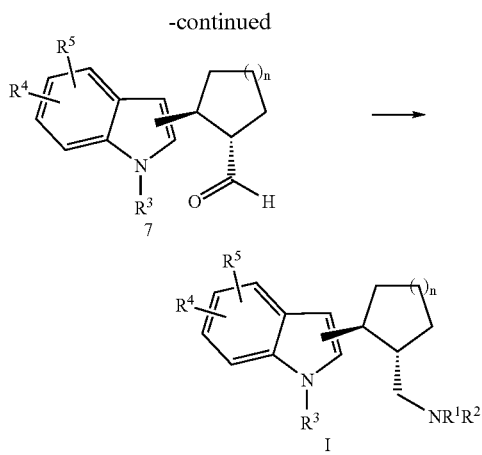

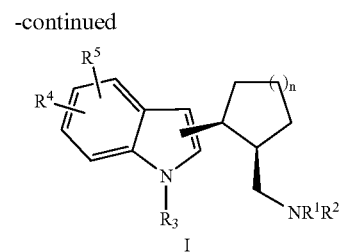

A preferred method of preparing cis-substituted compounds of Formula I is described in Scheme 3. The intermediate cis-disubstituted intermediate 5 is converted to the cis-carboxaldehyde 9 by methods known to those skilled in the art. One such method involves reduction of a carboxylic ester 5 to the corresponding alcohol 8 using reducing reagents such as lithium aluminum hydride, lithium borohydride, or the like. Oxidation of the alcohol 8 using reagents such as PCC, PDC, DMSO/oxalyl chloride, or the Dess-Martin periodinane, provides the cis-carboxaldehyde 9. The carboxaldehyde 9 is then reductively aminated with an appropriate amine using reducing reagents such as sodium cyanoborohydride, sodium triacetoxyborohydride, or the like, to give, after the removal of any protecting groups, the compound of Formula I.

Another preferred method of preparing compounds of Formula I is described in Scheme 4. An appropriately substituted indole carboxaldehyde 10 is condensed with an enolate or an enamine to give an alkylidine intermediate 11. Subsequent reduction of 11 using conditions such as catalytic hydrogenation, provides the ketone intermediate 12. Reductive amination of 12 under standard conditions provides the amines of Formula I.

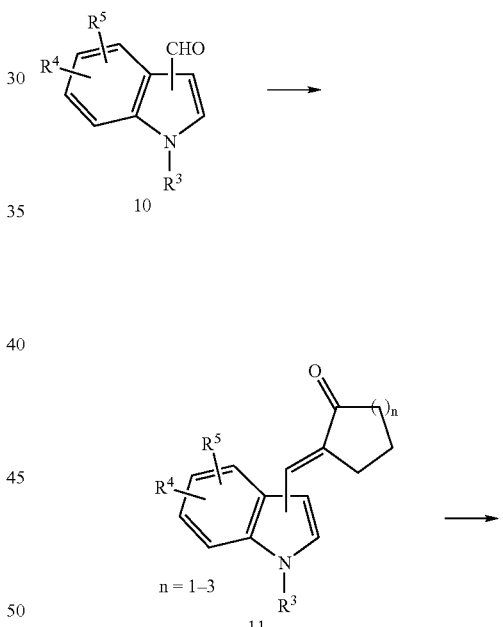

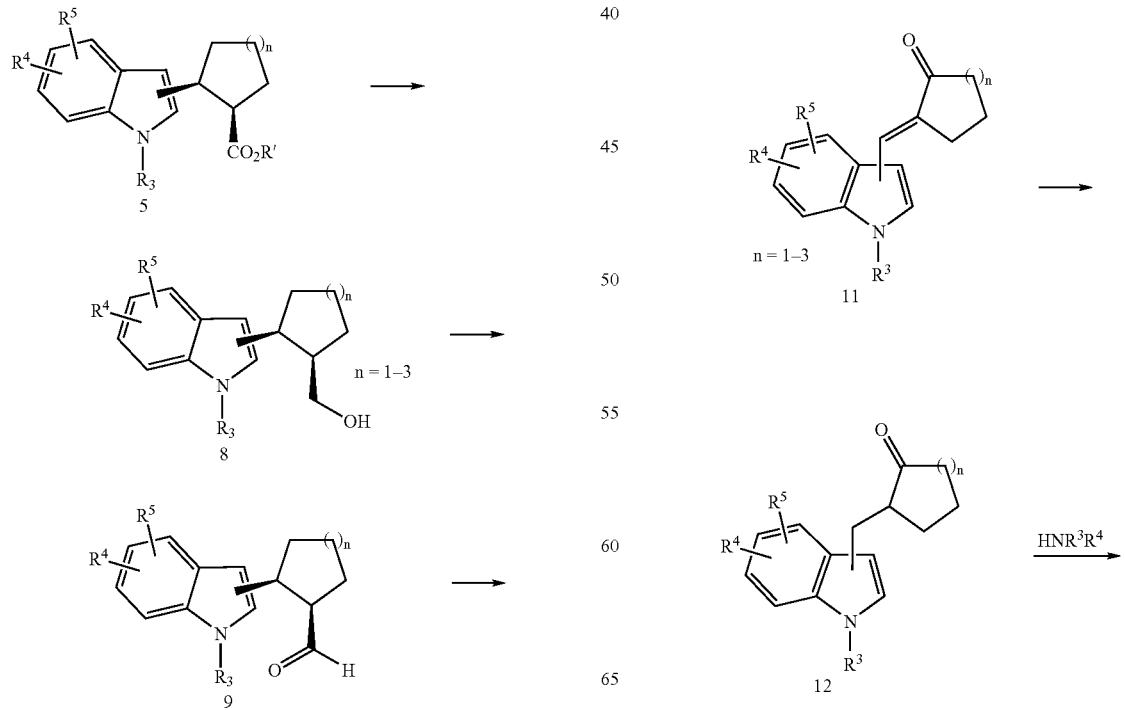

-continued

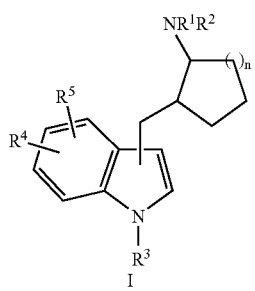

I

Synthetic Methods

LCMS Method

Unless otherwise noted, all products below were analyzed on a Shimadzu analytical high-performance liquid chromatography system equipped with a Micromass ESI mass spectrometer (positive ion mode). Elution was through a 3×50 mm YMC ODS-A C-18 S7 reverse phase column using the following gradient method: Start mobile phase composition: 10% methanol-90% water-0.1% trifluoroacetic acid; Final mobile phase composition: 90% methanol-10% water-0.1% trifluoroacetic acid; Gradient time=2 min; Hold time=1 min; Flow rate=5 mL/min; Wavelength=220 nm.

Synthesis of Intermediates

EXAMPLE 1

3-Iodo-1-(toluene-4-sulfonyl)-1H-indole-5-carbonitrile

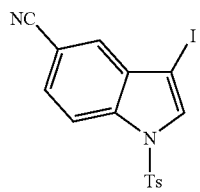

5-cyanoindole (4.0 g, 28.1 mMol) was dissolved in DMF (20 mL) and potassium hydroxide (4.74 g, 84.4 mMol) was added. The reaction was cooled in a water bath at 10° C. and iodine (7.12 g, 28.1 mMol) was added. After stirring for 30 min the reaction was poured into water (100 mL) with sodium thiosulfate (2 g). The resulting solid 5-cyano-3-iodo-lindole was collected by filtration and recrystallized from ethyl acetate and hexanes.

The crystals were dissolved in acetonitrile (60 mL) and N,N-diisopropylethylamine (5.64 mL, 32.3 mMol) and solid p-toluenesulfonyl chloride (6.17 g, 32.3 mMol) was added. After stirring for 1 h, the reaction was poured into water (100 mL) and the resulting solids were collected. The material was recrystallized from hot ethyl acetate/hexanes to provide the product as white needles (7.92 g, 67%): $^1$H NMR (400 MHz, CDCl$_3$) δ 8.06 (1H, d, J=9.2 Hz), 7.79 (3H, m), 7.73 (1H, d, J=1.5 Hz), 7.61 (1H, dd, J=8.6, 1.5 Hz), 7.29 (2H, d, J=8.5 Hz), 2.38 (3H, s); MS m/e 454.9 (M+Na).

EXAMPLE 2

1-(Toluene-4-sulfonyl)-3-tributylstannanyl-1H-indole-5-carbonitrile

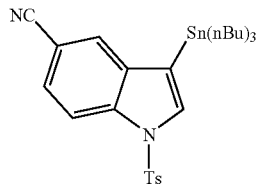

3-Iodo-1-(toluene-4-sulfonyl)-1H-indole-5-carbonitrile (5.0 g, 11.8 mMol) was added to a solution of bis(tributyltin) (6.27 mL, 12.4 mMol) in DMF (50 mL). Triphenyl phosphine (310 mg, 0.10 mMol) and palladium(II)acetate (133 mg, 0.59 mMol) were added and the reaction was heated to 60° C. for 40 min. The reaction was cooled in a water bath, then poured into brine (500 mL), and extracted with ethyl acetate (3×50 mL). The organic phase was dried with magnesium sulfate and the solvent was removed in vacuo. The reaction was purified by chromatography on silica gel with hexanes to remove tin byproducts followed by elution with ethyl acetate/hexanes (8%) to give the product as an off-white solid (5.67 g, 82%). $^1$H NMR (400 MHz, CDCl$_3$) δ 8.02 (1H, d, J=8.6 Hz), 7.75 (3H, m), 7.52 (1H, dd, J=8.6, 1.5 Hz), 7.49 (1H, s), 7.24 (2H, m), 2.35 (3H, s), 1.05–1.82 (18H, m), 0.89 (9H, m); MS m/e 587.3 (M+H).

EXAMPLE 3

2-Trifluoromethanesulfonyloxy-cyclopent-1-enecarboxylic acid ethyl ester

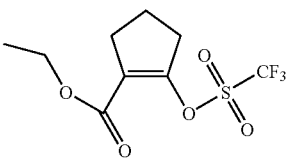

A solution of ethyl-2-oxocyclopentane-carboxylate (6.00 g, 38.4 mMol) in anhydrous tetrahydrofuran (50 mL) was treated with sodium hydride (60% mineral oil dispersion, 1.70 g, 42.3 mMol) and stirred at ambient temperature for 30 min. N-Phenyltrifluoromethanesulfonimide (15.1 g, 42.3 mMol) was added all at once, and stirring continued for 30 min. The mixture was carefully quenched with water, diluted with ethyl acetate, washed with brine, dried over sodium sulfate, and concentrated in vacuo to a hazy oil. Silica gel flash column chromatography (10% ethyl acetate/hexanes) gave the product as a clear oil which solidified upon standing (9.31 g, 84%). $^1$H-NMR (400 MHz, CDCl$_3$) δ 4.25 (2H, q, J=7.2 Hz), 2.71 (4H, m), 1.95 (2H, m), 1.31 (3H, J=7.2 Hz).

EXAMPLE 4

2-[5-Cyano-1-(toluene-4-sulfonyl)-1H-indol-3-yl]-cyclopent-1-enecarboxylic acid ethyl ester

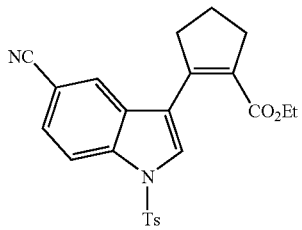

1-(Toluene-4-sulfonyl)-3-tributylstannanyl-1H-indole-5-carbonitrile (5.60 g, 9.56 mMol), 2-trifluoromethanesulfonyloxy-cyclopent-1-enecarboxylic acid ethyl ester (2.75 g, 9.56 mMol), triphenyl arsine (0.29 g, 0.96 mMol) and tris(dibenzylidenacetone)dipalladium(0) (0.44 g, 0.48 mMol) were dissolved in DMF and degassed for 5 min with a stream of nitrogen. The reaction was heated under nitrogen at 60° C. for 5 min. The reaction was poured into brine (500 mL) and extracted with ethyl acetate (2×100 mL). The organics were mixed with saturated aqueous potassium fluoride (100 mL) and the resulting solids were removed by filtration through celite. The layers of the filtrate were separated and the organic layer was dried with magnesium sulfate and evaporated in vacuo. The solid product was recrystallized from hot ethyl acetate/hexanes to provide the product as a white solid (3.04 g, 73%). $^1$H NMR (400 MHz, CDCl$_3$) δ 8.05 (1H, d, J=8.7 Hz), 7.87 (1H, s), 7.79 (2H, d, J=8.5 Hz), 7.71 (1H, d, J=1.2 Hz), 7.53 (1H, dd, J=8.8, 1.5 Hz), 7.27 (2H, m), 4.01 (2H, q, J=6.9 Hz), 2.86 (4H, m), 2.36 (3H, s), 2.03 (2H, pentet, J=7.7 Hz), 0.95 (3H, t, J=7.1 Hz); MS m/e 457.0 (M+Na).

EXAMPLE 5

2-(5-Cyano-1H-indol-3-yl)-cyclopent-1-enecarboxylic acid ethyl ester

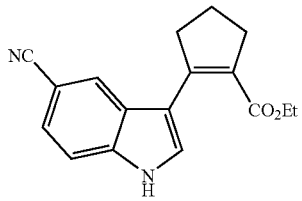

2-[5-Cyano-1-(toluene-4-sulfonyl)-1H-indol-3-yl]-cyclopent-1-enecarboxylic acid ethyl ester (2.0 g, 4.6 mMol) was dissolved in THF (100 mL) and sodium hydroxide (1.8 mL, 10 N, 18 mMol) was added. After refluxing for 4 h, the reaction was filtered through celite and the filtrate was evaporated. The residue was dissolved in brine (20 mL) and extracted with ethyl acetate (3×30 mL). The combined organics were dried with magnesium sulfate and evaporated in vacuo. The material was purified by chromatography on silica using ethyl acetate/hexanes (30–40%) as the eluent to provide the product as a white solid (1.21 g, 94%). $^1$H NMR (400 MHz, CDCl$_3$) δ 8.59 (1H, bs), 7.93 (1H, s), 7.84 (1H, s), 7.40 (2H, s), 4.12 (2H, q, J=7.2 Hz), 3.01 (2H, m), 2.86 (2H, m), 2.02 (2H, pentet, J=7.5 Hz), 1.16 (3H, t, J=7.3 Hz); MS m/e 303.2 (M+Na).

EXAMPLE 6 cis-2-(5-Cyano-1H-indol-3-yl)-cyclopentanecarboxylic acid ethyl ester

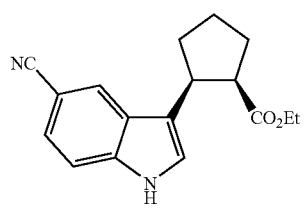

2-(5-Cyano-1H-indol-3-yl)-cyclopent-1-enecarboxylic acid ethyl ester (1.20 g, 4.3 mMol) was stirred and heated slightly until dissolved in methanol (250 mL). 10% palladium on carbon (300 mg) was added and the reaction was shaken in a Parr apparatus under hydrogen (50 psi) for 1 h. The reaction was filtered through Celite and sand, and the solvent was evaporated in vacuo. The product was obtained as a white solid (1.08 g, 89%). $^1$H NMR (400 MHz, CDCl$_3$) δ 8.31 (1H, bs), 8.00 (1H, s), 7.37 (2H, AB, δv=18 Hz, J=8.4 Hz), 7.09 (1H, d, J=1.5 Hz), 3.63 (2H, m), 3.48 (1H, m), 3.28 (1H, q, J=6.5 Hz), 2.00–2.22 (5H, m), 1.76 (1H, m), 0.63 (3H, t, J=6.8 Hz); MS m/e 305.2 (M+Na).

EXAMPLE 7

Mixture of cis/trans-2-(5-Cyano-1H-indol-3-yl)-cyclopentanecarboxylic acid methyl ester

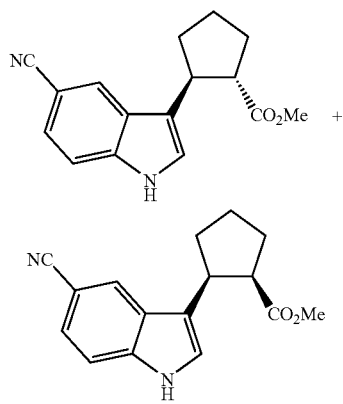

Sodium metal (13.5 g, 556 mMol) was carefully added portion-wise to anhydrous methanol (400 mL). A solution of cis-2-(5-cyanoindol-3-yl)-cyclopentanecarboxylic acid ethyl ester (33.1 g, 117 mMol) in methanol (100 mL) was added over 5 minutes. The mixture was heated at a gentle reflux for 18 hours, carefully quenched with water, and evaporated in vacuo. The residue was dissolved ethyl acetate (600 mL), washed with saturated sodium chloride (100 mL), dried over sodium sulfate, and concentrated in vacuo to give the product as an 88:12 cis/trans diastereomeric mixture which was used without further purification (27 g, 86%).

$^1$H NMR (400 MHz, CDCl$_3$) δ 8.42 (1H, bs), 7.96 (1H, m), 7.38 (2H, m), 7.13 (0.88H, m), 7.09 (0.12H, m), 3.62 (2.64H, m), 3.28 (0.12H, m), 3.14 (0.36H, s), 2.93 (0.88H, m), 2.28 (1H, m), 2.17 (1H, m), 1.99 (2H, m), 1.91 (2H, m), 1.80 (1H, m).

EXAMPLE 8

Enzymatic Resolution of trans-2-(5-Cyano-1H-indol-3-yl)-cyclopentanecarboxylic acid methyl ester

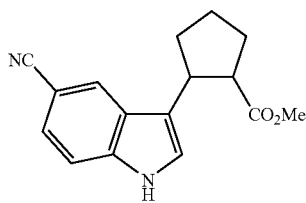

HPLC Assay Method A:

Column: YMC ODS-A (4.6×50 mm, S5). Isocratic elution with 1 mM HCl in water/MeCN (7/3) at 2 mL/min flow rate. UV monitored at 242 nm. Retention time: trans ester, 7.0 min; cis ester, 6.3 min; trans acid, 2.3 min.

HPLC Assay Method B:

Column: Chiralcel OD-RH (4.5×150 mm, S5). Gradient elution at 0.75 mL/min flow rate with 50 mM HClO$_4$ (solvent A) and MeCN (solvent B): 34% B for 13 min, 34–50% B in 1 min, 50% B for 8 min, 50–34% B in 1 min. UV monitored at 242 nm. Retention time: 1S,2S-trans acid, 12.9 min; 1R,2R-trans acid, 13.7 min; cis ester A, 20.1 min; cis ester B, 20.9 min; 1S,2S-trans ester, 21.3 min; 1R,2R-trans ester, 22.1 min.

(1R,2R)-2-(5-Cyano-1H-indol-3-yl)-cyclopentane-carboxylic acid

Sodium phosphate buffer (5.87 liter, 0.1 M, pH 7.2 @ 25° C.) was maintained at 50° C. in a 12 Liter jacketed reactor and stirred (200 rpm). Novozyme 435 (176 g, Novozymes North America Inc.) was added. The methyl ester cis/trans mixture (60 g, containing 51.86 g trans methyl ester and 6.84 g cis methyl ester) in DMSO (1 L) was added from an addition funnel over a period of 15 min. The suspension was stirred (200 rpm) at 50° C. for 3 days. The bead was collected by filtration and washed with 0.5 L water.

The filtrate and washes were combined and pH was adjusted to 10 with 10 N NaOH. The remaining ester in the filtrate was removed by MTBE washing (2×0.8 L). The pH of the aqueous layer was then adjusted to 2 with 6 N H$_2$SO$_4$, and the filtrate was extracted with MTBE (3×2 L). The MTBE extracts were combined, washed with water (3×0.2 L), and evaporated to give (1R,2R)-2-(5-cyano-1H-indol-3-yl)-cyclopentane-carboxylic acid as a yellow oil (27.2 g, purity: 98.9% by HPLC method A above, 100% ee by HPLC method B above). $^1$H NMR (400 MHz, CDCl$_3$) δ 8.40 (1H, bs), 7.98 (1H, s), 7.39 (2H, m), 7.18 (1H, m), 3.62 (1H, m), 2.95 (1H, m), 2.29 (1H, m), 2.20 (1H, m), 2.08 (1H, m), 1.92 (2H, m), 1.83 (1H, m).

(1S,2S)-2-(5-Cyano-1H-indol-3-yl)-cyclopentane-carboxylic acid

The ester from the above procedure was extracted from the bead with MeOH (2×1 L) followed with MTBE (2×2 L). The MeOH extract was evaporated to dryness and the residue was dissolved in MTBE (2 L) and 5% NaHCO$_3$ (1 L). The MTBE fractions were combined and washed with 0.1 M sodium carbonate buffer (pH 10.0, 5×0.2 L, and then with water (3×0.1 L). The MTBE layer was evaporated to give a cis/trans mixture of methyl esters as yellow oil (about 45 g, 78/20 trans/cis by HPLC method A above, (1S,2S)-trans ester: 98.8% ee by HPLC method B above).

Sodium phosphate buffer (5 L of 0.1 M, pH 7.8 @ 25° C.) was maintained at 50° C. in a 12 L jacketed reactor and stirred (330 rpm). Alcalase 2.4 L (1164 g, Novozymes North America Inc.) was added and pH was adjusted to 7.4 with 10 N NaOH. The cis/trans mixture of methyl esters was dissolved in DMSO (500 mL) and added from an addition funnel over a period of 30 min. Additional DMSO (500 mL) was added. The reaction was stirred for 1.5 hr at 50° C. and 4.5 hr at 40° C. After cooling to room temperature (25° C.), the pH was adjusted to 10.0 with 10 N NaOH. The reaction mixture was washed with MTBE (2×2 L). The aqueous layer was then adjusted to pH 2 with 6 N HCl, and then extracted with MTBE (3×2 L). The MTBE extracts were combined, washed with water (3×0.2 L), and evaporated to give (1S,2S)-2-(5-cyano-1H-indol-3-yl)-cyclopentane-carboxylic acid as light yellow solid (21.49 g, purity: 98.8% by HPLC method A, 100% ee by HPLC method B).

The remaining ester was recovered by evaporation of the initial MTBE extracts. The residue was dissolved in DMSO (300 mL) and added to a mixture of sodium phosphate buffer (1 L of 0.1 M, pH 7.8 @ 25° C.) and of Alcalase 2.4 L (50 mL, Novozymes North America Inc.) in a 2.8 liter flask at 40° C. The flask was stirred (200 rpm) at 40° C. for 18 hour, followed by standing at 25° C. overnight. The yellow solid floating on the reaction mixture was removed by filtration through two layers of milk filters. The pH was adjusted to 9.6 with 10 N NaOH, and the filtrate was washed with MTBE (2×0.15 L). The aqueous layer was adjusted to pH 2 with 6N HCl and extracted with MTBE (3×0.3 L). The MTBE extracts were combined, washed with water, and evaporated to give additional (1S,2S)-trans acid (2.27 g, purity: 99.9% by HPLC method A; 100% ee by HPLC method B). $^1$H NMR (400 MHz, CDCl$_3$) δ 8.35 (1H, bs), 7.98 (1H, s), 7.39 (2H, m), 7.18 (1H, d, J=2 Hz), 3.62 (1H, m), 2.94 (1H, m), 2.31 (1H, m), 2.20 (1H, m), 2.06 (1H, m), 1.92 (2H, m), 1.81 (1H, m).

The combined enzymatically resolved portions of (1S,2S)-2-(5-cyano-1H-indol-3-yl)-cyclo-pentane-carboxylic acid (22 g) were dissolved in 1N sodium hydroxide (500 mL) and washed with diethyl ether (1×100 mL). The aqueous solution was adjusted to pH<2 with concentrated hydrochloric acid and extracted with ethyl acetate (5×100 mL). The combined extracts were dried over sodium sulfate and concentrated in vacuo to give resolved (1S,2S)-2-(5-cyano-1H-indol-3-yl)-cyclopentane-carboxylic acid (20.5 g).

EXAMPLE 9 trans-2-(5-Cyano-1H-indol-3-yl)-cyclopentanecarboxylic acid methoxy-methyl-amide

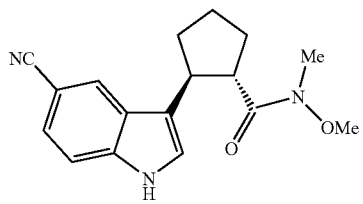

A solution of cis-2-(5-cyano-1H-indol-3-yl)-cyclopentanecarboxylic acid ethyl ester (1.06 g, 3.75 mMol) and lithium hydroxide monohydrate (1.54 g, 37.5 mMol) in ethanol (50 mL) and water (10 mL) was heated to reflux for 3 h. The solution was concentrated in vacuo, and the residue was dissolved in water (20 mL) and HCl was added to pH<2. The reaction was extracted with ethyl acetate (4×10 mL), dried with magnesium sulfate, and evaporated in vacuo. The residue was suspended in methylene chloride with triethylamine (2.62 mL, 18.8 mMol). To this was added N,O-dimethylhydroxylamine hydrochloride (733 mg, 7.5 mMol) and EDC hydrochloride (1.58 g, 8.26 mMol) and the reaction was stirred for 2 h. Water (20 mL) was added and the reaction was extracted with methylene chloride (10 mL). The organic layers were dried with magnesium sulfate and the solvent was evaporated in vacuo. The residue was purified by chromatography on silica gel with ethyl acetate/hexanes (60%) to provide the product as a clear oil (460 mg, 41%). $^1$H NMR (400 MHz, CDCl$_3$) δ 8.36 (1H, bs), 8.01 (1H, s), 7.28–7.41 (2H, m), 7.13 (1H, d, J=1.9 Hz), 3.74 (1H, m), 3.38 (3H, s), 3.38 (1H, buried), 3.11 (3H, s), 1.84–2.32 (5H, m), 1.37 (1H, sextet, J=7.6 Hz); MS m/e 320.2 (M+Na).

EXAMPLE 10 trans-3-(2-Formyl-cyclopentyl)-1H-indole-5-carbonitrile

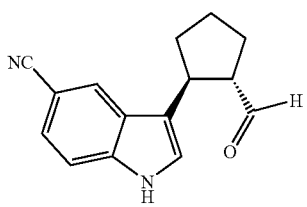

Trans-2-(5-cyano-1H-indol-3-yl)-cyclopentanecarboxylic acid methoxy-methyl-amide (460 mg, 1.5 mMol) was dissolved in THF and cooled to −40° C. Lithium aluminum hydride (117 mg, 3.1 mMol) was added and the temperature was maintained between −40 and −30° C. for 1 h. The reaction was quenched with ethyl acetate (10 mL) and warmed to 0° C. The reaction was treated dropwise with water (0.12 mL) and stirred 5 min. Then sodium hydroxide (1N, 0.36 mL) was added and the reaction was stirred 5 min. Then a further addition of water (0.12 mL) was made and the reaction was stirred for 20 min. The reaction was filtered through celite and sand, and the solvent was evaporated in vacuo. The residue was purified by chromatography on silica gel with ethyl acetate/hexanes (50%) to give the product as a clear oil (252 mg, 68%). $^1$H NMR (400 MHz, CDCl$_3$) δ 9.67 (1H, d, J=2.8 Hz), 8.37 (1H, brs), 7.96 (1H, s), 7.36–7.44 (2H, m), 7.14 (1H, d, J=2.3 Hz), 3.60 (1H, q, J=8.5 Hz), 2.98 (1H, q of d, J=7.5, 2.7 Hz), 2.30 (1H, m), 1.71–2.20 (5H, m); MS m/e 239.2 (M+H).

EXAMPLE 11

2-(3-Cyano-1H-indol-5-yl)-cyclopent-1-enecarboxylic acid ethyl ester

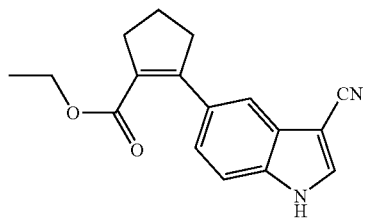

A solution of 5-bromo-3-cyanoindole (4.00 g, 18.1 mMol) in THF (20 mL) was added to a suspension of potassium hydride (2.28 g, 35% mineral oil dispersion, 19.9 mMol) in anhydrous THF (50 mL) at 0° C. After stirring for 15 min, the solution was cooled to −78° C., whereupon some precipitation occurred. A solution of n-butyllithium (2.5 M in hexanes, 16 mL) was slowly added via syringe. The resulting mixture was stirred at −78° C. for 15 minutes and then tributylborate (9.16 g, 39.8 mMol) was added. The mixture was removed from the cooling bath, stirred for 15 minutes, carefully quenched with water, and concentrated in vacuo. The residue was vigorously mixed with 1 N hydrochloric acid and extracted three times with ethyl acetate. The ethyl acetate layers were extracted three times with 1 N sodium hydroxide. The combined aqueous extracts were made acidic with concentrated hydrochloric acid to give 3-cyano-5-indolylboronic acid as a light tan precipitate which was collected by filtration and dried under vacuum (1.82 g, 55%). $^1$H-NMR (400 MHz, DMSO) δ 12.19 (1H, br s), 6.05 (1H, d, J=5.2 Hz), 8.24 (1H, d, J=2.8 Hz), 8.17 (1H, d, 6.4 Hz), 7.69 (1H, d, J=8.2 Hz), 7.49 (1H, d, J=8.2 Hz).

A mixture of 5-(3-cyanoindolyl)boronic acid (0.82 g, 4.4 mMol), 2-trifluoromethanesulfonyloxy-cyclopent-1-enecarboxylic acid ethyl ester (2.5 g, 8.8 mMol), tetrakis(triphenylphosphine)palladium(0) (0.50 g, 0.44 mMol), sodium bicarbonate (1.11 g, 13.2 mMol), ethylene glycol dimethyl ether (25 mL), and water (10 mL) was stirred at reflux under nitrogen for 18 h. The mixture was cooled to room temperature and filtered. The filtrate was concentrated and the residue dissolved in ethyl acetate, washed with brine, dried over sodium sulfate and evaporated to dryness. Silica gel flash column chromatography (50% ethyl acetate/hexanes) gave the product as a brown oil which solidified upon standing (0.97 g, 78%). $^1$H-NMR (400 MHz, CDCl$_3$) δ 8.91 (1H, br s), 7.66 (1H, s), 7.59 (1H, d, J=2.8 Hz), 7.25 (2H, m), 4.12 (2H, m), 2.88 (4H, m), 2.02 (2H, m), 1.18 (3H, t, J=7 Hz).

EXAMPLE 12 cis-2-(3-Cyano-1H-indol-5-yl)-cyclopentanecarboxylic acid ethyl ester

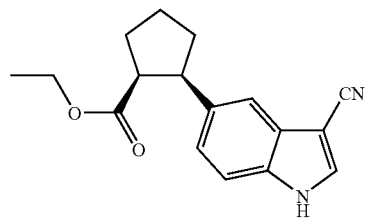

A solution of 2-(3-cyano-1H-indol-5-yl)-cyclopent-1-enecarboxylic acid ethyl ester (0.97 g, 3.46 mMol) in methanol (50 mL) was treated with 10% palladium(0) on carbon (0.35 g) and hydrogenated at 50 psi in a Parr apparatus for 22 h. The mixture was filtered through Celite® 545 and concentrated in vacuo to give the product as a clear oil which solidified upon standing (0.95 g, 97%). $^1$H-NMR (500 MHz, CDCl$_3$) δ 8.76 (1H, br s), 7.65 (1H, d, J=2.0 Hz), 7.60 (1H, s), 7.25 (1H, d, J=8.5 Hz), 7.18 (1H, m), 3.71 (2H, m), 3.57 (1H, m), 3.21 (1H, m), 2.16 (m, 4H), 2.02 (1H, m), 1.78 (1H, m), 0.85 (3H, t, J=7.0 Hz).

EXAMPLE 13 trans-2-(3-Cyano-1H-indol-5-yl)-cyclopentanecarboxylic acid

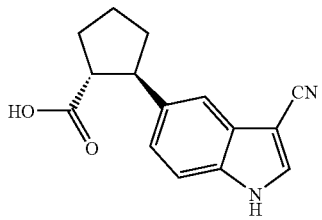

A solution of cis-2-(3-Cyano-1H-indol-5-yl)-cyclopentanecarboxylic acid ethyl ester (0.95 g, 3.36 mMol), lithium hydroxide monohydrate (0.71 g, 16.8 mMol), methanol (20 mL), and water (5 mL) was heated at reflux for 6 h. The solution was concentrated in vacuo and the residue dissolved in water and washed once with dichloromethane. The aqueous layer was acidified with concentrated hydrochloric acid and extracted with ethyl acetate (3×20 mL). The pooled organic extracts were washed once with brine, dried over sodium sulfate, and concentrated in vacuo to give the product as a light brown oil which solidified upon standing (0.66 g, 77%). LC-MS: 1.33 min (2 min gradient); 277.07 (MNa)$^+$.

EXAMPLE 14 trans-2-(3-Cyano-1H-indol-5-yl)-cyclopentanecarboxylic acid methoxy-methyl-amide

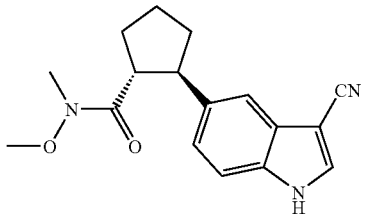

A mixture of trans-2-(3-Cyano-1H-indol-5-yl)-cyclopentanecarboxylic acid (0.66 g, 2.60 mMol), N,O-dimethylhydroxylamine hydrochloride (0.51 g, 5.20 mMol), 1-(3-dimethylaminopropyl)-3-ethylcarbodiimide hydrochloride (0.54 g, 2.86 mMol), and dichloromethane (20 mL) was treated with triethylamine (1.05 g, 10.4 mMol) and stirred at ambient temperature for 18 h. The resulting solution was diluted with 30 mL dichloromethane, washed with 1M hydrochloric acid, 1M sodium hydroxide, and brine, dried over sodium sulfate and concentrated in vacuo to give the crude product as a clear oil which was used without further purification (0.51 g, 66%). LC-MS: 1.38 min (2 min gradient); 298.11 (MH)$^+$.

EXAMPLE 15 trans-5-(2-Formyl-cyclopentyl)-1H-indole-3-carbonitrile

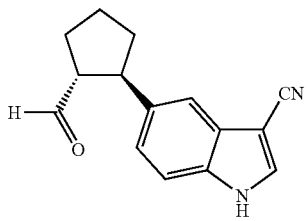

A solution of trans-2-(3-cyano-1H-indol-5-yl)-cyclopentanecarboxylic acid methoxy-methyl-amide (0.50 g, 1.68 mMol) in anhydrous tetrahydrofuran (15 mL) was cooled to −45° C. and treated with lithium aluminum hydride (0.13 g, 1.68 mMol). The mixture was stirred for 30 min and then treated with an additional 2 equivalents reducing agent (0.13 g, 1.68 mMol). Stirred at −45° C. for 30 min, quenched with 1M hydrochloric acid, filtered through sand and concentrated the filtrate in vacuo. Silica gel flash column chromatography (50% ethyl acetate/hexanes) gave the product as a colorless oil (0.30 g, 73%). $^1$H-NMR (500 MHz, CDCl$_3$) δ 9.69 (1H, d, J=2.5 Hz), 8.73 (1H, br s), 7.67 (1H, d, J=2.5 Hz), 7.62 (1H, s), 7.36 (1H, d, J=8 Hz), 7.18 (1H, m), 3.44 (1H, m), 2.93 (1H, m), 2.24 (1H, m), 2.05 (2H, m), 1.95 (1H, m), 1.88 (1H, m), 1.78 (1H, m).

EXAMPLE 16 trans-5-(2-Formyl-cyclopentyl)-1-methyl-1H-indole-3-carbonitrile

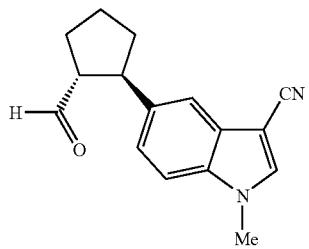

A solution of trans-2-(3-Cyano-1-methyl-1H-indol-5-yl)-cyclopentanecarboxylic acid methoxy-methyl-amide (0.080 g, 0.27 mMol) in anhydrous tetrahydrofuran (5 mL) was treated with sodium hydride (0.013 g, 1.68 mMol). The mixture was stirred for 15 minutes and then treated with iodomethane (0.077 g, 0.54 mMol). After stirring 1.5 hours, the mixture was quenched with water and evaporated. The residue was dissolved in ethyl acetate, washed with brine, dried over sodium sulfate, filtered, and concentrated in vacuo to give a hazy oil. This residue was dissolved in anhydrous tetrahydrofuran (5 mL), cooled to −45° C., and treated with lithium aluminum hydride (0.021 g, 0.54 mMol). The suspension was stirred for 2 hours and then quenched in the usual manner. The resulting mixture was filtered over sand and concentrated in vacuo. Silica gel flash column chromatography (50% hexanes, ethyl acetate) gave the product as a clear oil (0.064 g, 76%). LC-MS: 1.39 min (2 min gradient); 312.21 (MH)$^+$.

EXAMPLE 17 cis-5-(2-Hydroxymethyl-cyclopentyl)-1H-indole-3-carbonitrile

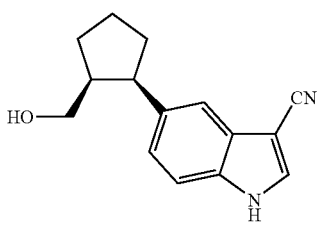

A 0° C. solution of cis-2-(3-Cyano-1H-indol-5-yl)-cyclopentanecarboxylic acid ethyl ester (0.90 g, 3.19 mMol) in tetrahydrofuran (40 mL) was treated with lithium aluminum hydride (0.24 g, 6.38 mMol) and stirred for 2 h. An additional 2 equivalents lithium aluminum hydride (0.24 g, 6.38 mMol) were added, and the reaction was warmed to 15° C. After 2 h at that temperature, the reaction was quenched with 1M hydrochloric acid, stirred for 30 min, filtered through sand, dried over sodium sulfate, and concentrated by rotary evaporation. Silica gel flash column chromatography (50% ethyl acetate/hexanes) gave the product as a white foam (0.58 g, 76%). $^1$H-NMR (CDCl$_3$) δ 8.74 (1H, br s), 7.70 (1H, m), 7.59 (1H, s), 7.36 (1H, J=8.8 Hz), 7.22 (1H, m), 3.42 (1H, m), 3.31–3.24 (2H, m), 2.80 (1H, m), 2.45 (1H, m), 2.04 (1H, m), 1.96 (m, 3H), 1.75 (1H, m), 1.58 (1H, m).

EXAMPLE 18 cis-5-(2-Formyl-cyclopentyl)-1H-indole-3-carbonitrile

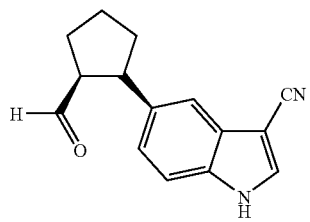

A solution of cis-5-(2-Hydroxymethyl-cyclopentyl)-1H-indole-3-carbonitrile (0.58 g, 2.41 mMol) in anhydrous dichloromethane (10 mL) at 0° C. was treated with Dess-Martin periodinane (1.54 g, 3.62 mMol) and stirred for 2 h. The solution was warmed to ambient temperature, stirred for 18 h, washed once with 1M sodium hydroxide and brine, dried over sodium sulfate and evaporated to dryness. Silica gel flash column chromatography (50% ethyl acetate/hexanes) gave the product as a clear oil (0.134 g, 23%). $^1$H-NMR (500 MHz, CDCl$_3$) δ 9.28 (1H, d, J=2.5 Hz), 8.72 (1H, br s), 7.68 (1H, d, J=2.5 Hz), 7.63 (1H, d, J=0.5 Hz), 7.34 (1H, d, 8.5 Hz), 7.16 (1H, dd, J=8.5, 1.5 Hz), 3.67 (1H, m), 3.16 (1H, m), 2.20 (m, 2H), 2.05–1.98 (3H, m), 1.80 (m, 1H). LC-MS: 1.33 min (2 min gradient); 261.26 (MNa)$^+$.

EXAMPLE 19 trans-3-(2-Formyl-cyclopentyl)-1-methyl-1H-indole-5-carbonitrile

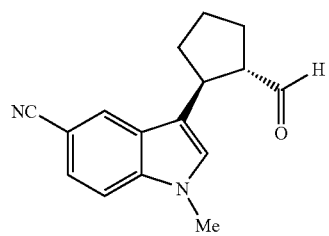

A solution of trans-2-(5-Cyano-1-methyl-1H-indol-3-yl)-cyclopentanecarboxylic acid methoxy-methyl-amide (0.25 g, 0.84 mMol) in anhydrous tetrahydrofuran (15 mL) was treated with sodium hydride (0.067 g, 1.68 mMol). The mixture was stirred for 15 minutes and then treated with iodomethane (0.36 g, 2.52 mMol). After stirring 1.5 hours, the mixture was quenched with water and evaporated. The residue was dissolved in ethyl acetate, washed with brine, dried over sodium sulfate, filtered, and concentrated in vacuo to give a hazy oil. This residue was dissolved in anhydrous tetrahydrofuran (5 mL), cooled to −45° C., and treated with lithium aluminum hydride (0.060 g, 1.57 mMol). The suspension was stirred for 1 hour and then quenched in the usual manner. The resulting mixture was filtered over sand and concentrated in vacuo. Silica gel flash column chromatography (50% hexanes, ethyl acetate) gave the product as a clear oil. ¹H-NMR (400 MHz, CDCl₃) δ 9.66 (1H, d, J=2.8 Hz), 7.94 (1H, m), 7.44 (1H, m), 7.42 (1H, m), 6.99 (1H, s), 3.76 (3H, s), 3.61 (1H, m), 2.98 (1H, m), 2.22 (1H, m), 2.02 (2H, m), 1.98 (1H, m), 1.87 (2H, m).

EXAMPLE 20 trans-3-(2-Formyl-cyclopentyl)-1-ethyl-1H-indole-5-carbonitrile

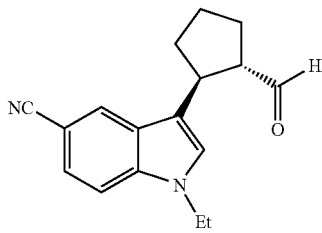

Trans-3-(2-Formyl-cyclopentyl)-1-ethyl-1H-indole-5-carbonitrile was prepared in a manner similar to Example 20. ¹H NMR (400 MHz, CDCl₃) δ 9.65 (1H, d, J=3.2 Hz), 7.94 (1H, m), 7.41 (1H, m), 7.34 (1H, m), 7.05 (1H, s), 4.12 (2H, q, J=7.6 Hz), 3.57 (1H, m), 2.95 (1H, m), 2.28 (1H, m), 2.04 (2H, m), 1.91 (1H, m), 1.82 (2H, m), 1.44 (3H, t, J=7.5 Hz).

EXAMPLE 21

3-(2-Oxo-cyclopentylmethyl)-1H-indole-5-carbonitrile

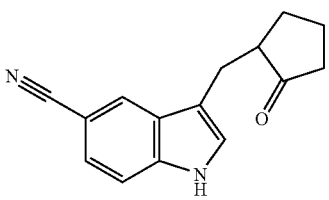

A solution of 3-formyl-1-(toluene-4-sulfonyl)-1H-indole-5-carbonitrile (6.0 g, 18.5 mMol) and 4-(1-cyclopentenyl) pyrrolidine (3.05 g, 22.2 mMol) in benzene (200 mL) containing p-toluenesufonic acid (100 mg) were heated to reflux with azeotropic removal of water for 2 h. The solution was cooled and concentrated to dryness. The residue was then dissolved in THF (100 mL) and methanol (50 mL) and 6 N HCl (100 mL) was added dropwise with stirring over 15 min. The solution was stirred for 48 h and concentrated in vacuo. The residue was dissolved in chloroform/methanol (9:1), extracted with brine (3×250 mL), and dried over Na₂SO₄. The solution was concentrated and the residue was purified by silica gel column chromatography (20% ethyl acetate/hexanes-90% ethyl acetate/hexanes) to give 3-(2-oxo-cyclopent-ylidenemethyl)-1-(toluene-4-sulfonyl)-1H-indole-5-carbonitrile (3.0 g, 42%). ¹H NMR (400 MHz, CDCl₃) δ 8.07 (2H, d, J=6.4 Hz), 7.85 (1H, s), 7.80 (2H, d, J=6.8 Hz), 7.61 (1H, dd, J=8.8 Hz, 1.2 Hz), 7.46 (1H, t, J=2.8 Hz), 7.29 (2H, d, J=8.0 Hz), 2.91 (2H, m), 2.47 (2H, m), 2.37 (3H, s), 2.12 (2H, m); MS m/e 391 (M+H)⁺.

Water (50 mL) and sodium hydroxide (50 mL, 10 N) were added to a solution of 3-(2-oxo-cyclopentylmethyl)-1-(toluene-4-sulfonyl)-1H-indole-5-carbonitrile (1.0 g, 2.56 mMol) in THF (200 mL), and the mixture was stirred for 16 h. The reaction was diluted with ethyl acetate (300 mL), quenched with 1N HCl (100 mL), and then poured into a mixture of saturated aqueous sodium bicarbonate (200 mL) and brine (100 mL). The aqueous layer was extracted with ethyl acetate (4×250 mL). The combined organic layers were washed with brine (150 mL), dried over Na₂SO₄, and concentrated in vacuo. The crude material was purified by silica gel chromatography using a step gradient of 20% ethyl acetate/hexanes-85% ethyl acetate/hexanes to give 3-(2-oxo-cyclopentylidenemethyl)-1H-indole-5-carbonitrile as a yellow solid (400 mg, 67%) after drying under vacuum. ¹H NMR (400 MHz, DMSO-d₆) δ 8.43 (1H, s), 7.96 (1H, m), 7.63 (2H, m), 7.55 (1H, m), 2.85 (2H, m), 2.35 (2H, m), 2.00 (2H, m); LCMS (4.6×50 mm XTERRA C-18 S5 column, 5 mL/min, 0–100% MeOH/H₂O/0.1% TFA, 2 min gradient): T$_r$=1.50 min, m/e 237 (M+H)⁺.

A solution of 3-(2-oxo-cyclopentylidenemethyl)-1H-indole-5-carbonitrile (800 mg, 3.39 mMol) in methanol (120 mL) was hydrogentated at atmospheric pressure for 16 h over 10% Pd/C catalyst (300 mg). The mixture was filtered and the filtrate was concentrated in vacuo. The residue was purified by silica gel chromatography (5% ethyl acetate/hexanes-80% ethyl acetate/hexanes) to give 3-(2-oxo-cyclopentylmethyl)-1H-indole-5-carbonitrile (140 mg, 18%). LCMS (4.6×50 mm XTERRA C-18 S5 column, 5 mL/min, 0–100% MeOH/H₂O/0.1% TFA, 2 min gradient): T$_r$=1.51 min, m/e 261 (M+H+Na)⁺.

EXAMPLE 22

(+/−) trans-3-(2-acetylcyclopentyl)-1H-indole-5-carbonitrile

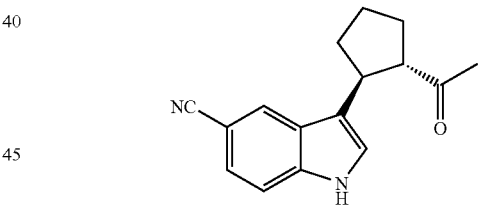

(+/−) Trans-3-(2-formylcyclopentyl)-1H-indole-5-carbonitrile (0.50 g, 2.1 mMol) at 0° C. in anhydrous tetrahydrofuran (20 mL) was treated with methylmagnesium chloride (0.77 mL, 3M in THF, 2.3 mMol). The resulting mixture was stirred for 30 min at 0° C. and then quenched with 1 N aqueous HCl (10 mL). The solution was poured into water (20 mL) and extracted with ethyl acetate (50 mL). The organic layer was dried with magnesium sulfate and evaporated in vacuo. The material was partially purified by silica gel column chromatography (40% ethyl acetate in hexanes) to obtain 200 mg of intermediate.

The resulting residue was dissolved in methylene chloride and cooled to 0° C. Dess-Martin periodinane (500 mg, 1.18 mMol) was added and the reaction was stirred at 0° C. for 1 hour. The reaction was washed with aqueous sodium bicarbonate (2×20 mL), dried with magnesium sulfate and the solvent was removed in vacuo. The residue was purified by silica gel column chromatography (3:1 hexanes/ethyl acetate) to give (+/−) trans-3-(2-acetylcyclopentyl)-1H-indole-5-carbonitrile (72 mg, 14%): $^1$H NMR (400 MHz, CDCl$_3$) δ 8.23 (1H, brs), 7.98 (1H, s), 7.35–7.45 (2H, m), 7.13 (1H, d, J=2.4 Hz), 3.60 (1H, q, J=8.3 Hz), 3.14 (1H, q, J=7.7 Hz), 2.07 (3H, s), 1.75–2.25 (6H, m); MS m/e 275.2 (M+Na)$^+$.

EXAMPLE 23

(+/−) trans-3-(2-propionylcyclopentyl)-1H-indole-5-carbonitrile

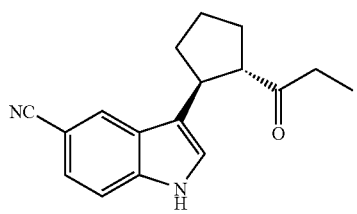

(+/−) Trans-3-(2-formylcyclopentyl)-1H-indole-5-carbonitrile (0.56 g, 2.4 mMol) at 0° C. in anhydrous tetrahydrofuran (20 mL) was treated with ethylmagnesium bromide (2.82 mL, 1M in THF, 2.8 mMol). The resulting mixture was stirred for 30 min at 0° C. and then quenched with 1 N aqueous HCl (5 mL). The solution was poured into water (20 mL) and extracted with ethyl acetate (50 mL). The organic layer was dried with magnesium sulfate and evaporated in vacuo. The material was partially purified by silica gel column chromatography (40% ethyl acetate in hexanes) to obtain 200 mg of intermediate.

The resulting residue was dissolved in methylene chloride and cooled to 0° C. Dess-Martin periodinane (500 mg, 1.18 mMol) was added and the reaction was stirred at 0° C. for 1 hour. The reaction was washed with aqueous sodium bicarbonate (2×20 mL), dried with magnesium sulfate and the solvent was removed in vacuo. The residue was purified by silica gel column chromatography (3:1 hexanes/ethyl acetate) to give (+/−) trans-3-(2-propionylcyclopentyl)-1H-indole-5-carbonitrile (40 mg, 6%): $^1$H NMR (400 MHz, CDCl$_3$) δ 8.31 (1H, brs), 7.96 (1H, s), 7.42 (2H, m), 7.11 (1H, d, J=2.4 Hz), 3.60 (1H, q, J=8.0 Hz), 3.14 (1H, q, J=8.2 Hz), 1.50–2.43 (8H, m), 0.95 (3H, t, J=7.6 Hz); MS m/e 267.2 (M+H)$^+$.

EXAMPLE 24

Trans (1S,2S)-2-(5-iodo-1H-indol-3-yl)-cyclopentanecarboxaldehyde

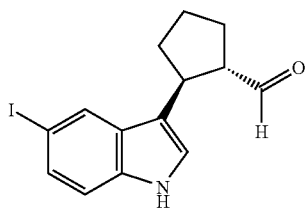

(2S,5S)-5-Benzyl-3-methyl-2-(5-methyl-furan-2-yl)-imidazolidin-4-one was prepared by literature methods [Journal of the American Chemical Society (2002), 124(11), 2458–2460; PCT Int. Appl. (2003), WO 0347740 A2 20030612]. Trifluoroacetic acid (0.63 mL, 8.2 mMol) was added with stirring to a −35° C. solution of 1-cyclopentene-1-carboxaldehyde (12 g, 125 mMol) and (2S,5S)-5-benzyl-3-methyl-2-(5-methyl-furan-2-yl)-imidazolidin-4-one (2.2 g, 8.2 mMol) in dichloromethane/isopropanol (80 mL, 85/15). After the resulting mixture was stirred for ~15 min, 5-iodoindole (20 g, 82 mMol) in dichloromethane/isopropanol (80 mL, 85/15) was added. The reaction was stirred between −30° C. and −25° C. for ~18 h. The reaction was diluted with 400 mL of dichloromethane and washed with aqueous NaHCO$_3$ (400 mL), 1N HCl (2×200 mL), and brine (2×200 mL) (The aqueous layer was re-extracted each time with 40 mL of dichloromethane and the extract was combined with organic layer). The organic layer was dried over MgSO$_4$ and solvent was removed under vacuum. The crude product was then purified by silica gel chromatography using hexane/ethyl acetate (100/0 to 80/20) as the eluent to give trans (1S,2S)-2-(5-iodo-1H-indol-3-yl)-cyclopentanecarbaldehyde (21 g, 75%, ~80% ee). This material was crystallized from ethyl acetate/hexane (12 g, >98% ee). $^1$H NMR (400 MHz, acetonitrile-d$_3$) δ 9.64 (d, 1H), 9.23 (b, 1H), 7.98 (s, 1H), 7.42 (d, 1H), 7.27 (d, 1H), 7.13 (d, 1H), 3.55 (m, 1H), 2.94 (m, 1H), 2.12 (m, 1H), 2.1–1.7 (m, 5H); $^{13}$C NMR (400 MHz, acetonitrile-d$_3$), δ 204.2, 163.0, 130.1, 129.8, 128.1, 122.8, 117.4, 114.2, 82.1, 48.5, 38.2, 34.5, 26.5, 25.0; HRMS (EI), exact mass calc'd for C$_{14}$H$_{14}$INO (M−H) 338.0042, found 338.0048.

Synthesis of Compounds of Formula I

EXAMPLE 25

Trans-3-(2-dimethylaminomethyl-cyclopentyl)-1H-indole-5-carbonitrile

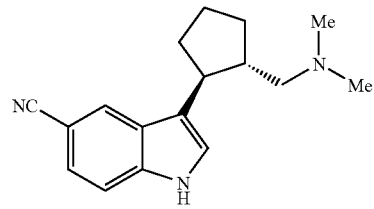

Trans-3-(2-formyl-cyclopentyl)-1H-indole-5-carbonitrile (200 mg, 0.84 mMol) was stirred in THF (5 mL) and methanol (30 mL) with dimethylamine (0.84 mL, 2M in THF, 1.68 mMol) for 5 min. Sodium triacetoxyborohydride (530 mg, 2.52 mMol) was added and the reaction was stirred a further 30 min. The solvent was evaporated in vacuo and the residue was dissolved in 1N sodium hydroxide (20 mL). The reaction was extracted with ethyl acetate (3×10 mL), dried with magnesium sulfate, and evaporated to a white powder. The material was purified by precipitation from hot methylene chloride to provide the product (144 mg, 64%). $^1$H NMR (400 MHz, CDCl$_3$) δ 8.32 (1H, brs), 8.00 (1H, s), 7.39 (2H, m), 7.12 (1H, d, J=1.8 Hz), 2.90 (1H, m), 2.17 (6H, s), 2.06–2.33 (5H, m), 1.66–1.90 (3H, m), 1.49 (1H, m); MS m/e 268.2 (M+H).

EXAMPLE 26

Trans-3-(2-methylaminomethyl-cyclopentyl)-1H-indole-5-carbonitrile

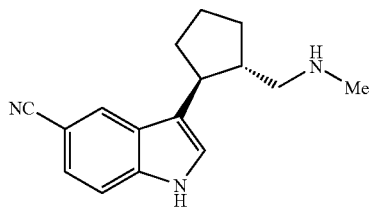

Trans-3-(2-methylaminomethyl-cyclopentyl)-1H-indole-5-carbonitrile was prepared in a manner similar to Example 22. The material was purified by chromatography on silica gel with a 9:1 mixture of chloroform/2M ammonia in methanol to provide trans-2-[5-cyanoindol-3-yl]-1-(N-methylaminomethyl)-cyclopentane as a white solid (6 mg, 71%). LC-MS: 1.06 min (2 min gradient); 254.20 (MH)+.

EXAMPLE 27

Trans-3-(2-ethylaminomethyl-cyclopentyl)-1H-indole-5-carbonitrile

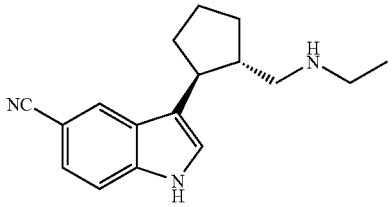

Trans-3-(2-ethylaminomethyl-cyclopentyl)-1H-indole-5-carbonitrile was prepared (5 mg, 56%) by the method given in Example 22. LC-MS: 1.06 min (2 min gradient); 268.3 (MH)+.

EXAMPLE 28

Trans-3-(2-diethylaminomethyl-cyclopentyl)-1H-indole-5-carbonitrile

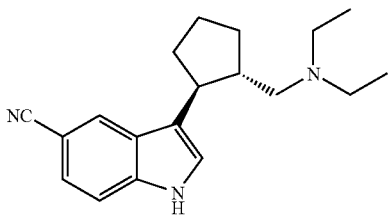

Trans-3-(2-diethylaminomethyl-cyclopentyl)-1H-indole-5-carbonitrile was prepared (8.5 mg, 85%) by the method given in Example 22. LC-MS: 1.07 min (2 min gradient); 296.3 (MH)+.

EXAMPLE 29

Trans-3-{2-[(ethyl-methyl-amino)-methyl]-cyclopentyl}-1H-indole-5-carbonitrile

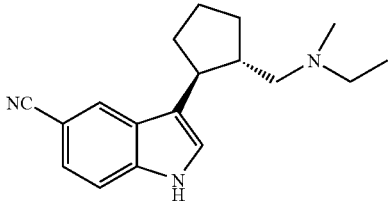

Trans-3-{2-[(ethyl-methyl-amino)-methyl]-cyclopentyl}-1H-indole-5-carbonitrile was prepared (6.9 mg, 69%) by the method given in Example 22. LC-MS: 1.02 min (2 min gradient); 282.3 (MH)+.

EXAMPLE 30

Trans-3-(pyrrolidin-1-ylmethyl-cyclopentyl)-1H-indole-5-carbonitrile

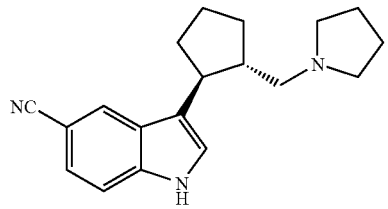

Trans-3-(pyrrolidin-1-ylmethyl-cyclopentyl)-1H-indole-5-carbonitrile was prepared (8.7 mg, 88%) by the method given in Example 22. LC-MS: 1.02 min (2 min gradient); 294.3 (MH)+.

EXAMPLE 31

Trans-3-{2-[(benzyl-methyl-amino)-methyl]-cyclopentyl}-1H-indole-5-carbonitrile

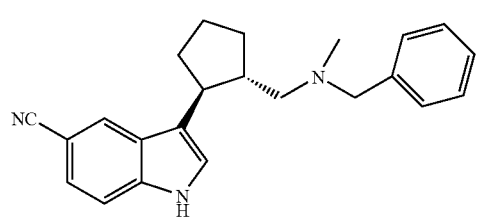

Trans-3-{2-[(benzyl-methyl-amino)-methyl]-cyclopentyl}-1H-indole-5-carbonitrile was prepared (11 mg, 95%) by the method given in Example 22. LC-MS: 1.21 min (2 min gradient); 344.3 (MH)+.

EXAMPLE 32

Trans-3-(2-dimethylaminomethyl-cyclopentyl)-1-methyl-1H-indole-5-carbonitrile

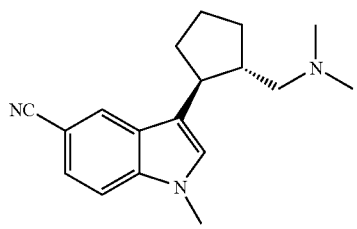

Trans-3-(2-dimethylaminomethyl-cyclopentyl)-1-methyl-1H-indole-5-carbonitrile was prepared (84 mg, 61%) from trans-3-(2-formyl-cyclopentyl)-1-methyl-1H-indole-5-carbonitrile by the method described in Example 22. LC-MS: 1.11 (2 min gradient); 282.25 (MH)$^+$.

EXAMPLE 33

Trans-3-(2-dimethylaminomethyl-cyclopentyl)-1-ethyl-1H-indole-5-carbonitrile

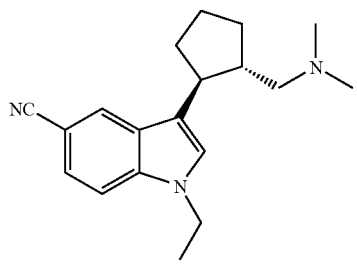

Trans-3-(2-dimethylaminomethyl-cyclopentyl)-1-ethyl-1H-indole-5-carbonitrile was prepared (160 mg, 44%) from trans-3-(2-formyl-cyclopentyl)-1-ethyl-1H-indole-5-carbonitrile by the method described in Example 22. LC-MS: 1.17 (2 min gradient); 296.27 (MH)$^+$.

EXAMPLE 34

Trans-5-(2-dimethylaminomethyl-cyclopentyl)-1H-indole-3-carbonitrile

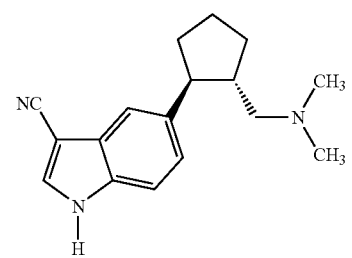

A solution of trans-5-(2-formyl-cyclopentyl)-1H-indole-3-carbonitrile (0.294 g, 1.23 mMol), dimethylamine (2.0M in tetrahydrofuran, 3 mL) and 5 mL methanol was treated with sodium triacetoxyborohydride (1.3 g, 6.17 mMol) and stirred at ambient temperature for 1 h. The solvent was removed in vacuo and the residue partitioned in ethyl acetate and 1M sodium hydroxide. The aqueous layer was extracted several times with additional ethyl acetate, and the pooled organic layers were dried over sodium sulfate and concentrated to dryness. Silica gel flash column chromatography (10% 2M ammonia in methanol/chloroform) gave the product as a white solid (0.115 g, 35%). $^1$H-NMR (400 MHz, DMSO) δ 12.1 (1H, br s), 8.18 (1H, s), 7.46 (1H, d, J=8.4 Hz), 7.42 (1H, s), 7.18 (1H, m), 3.17 (2H, m), 2.67 (1H, m), 2.20–1.98 (3H, m), 2.00 (6H, m), 1.78 (1H, m), 1.72 (2H, m), 1.45 (1H, m). LC-MS: 0.98 min (2 min gradient); 268.26 (MH)$^+$.

EXAMPLE 35

Trans-5-(2-methylaminomethyl-cyclopentyl)-1H-indole-3-carbonitrile

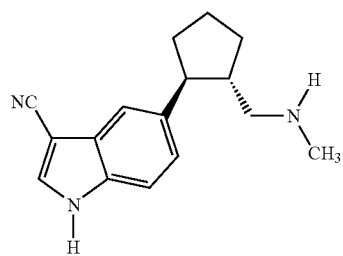

Trans-5-(2-methylaminomethyl-cyclopentyl)-1H-indole-3-carbonitrile was prepared (4.3 mg, 19%) by the method given in Example 31. LC-MS: 1.00 min (2 min gradient); 254.20 (MH)$^+$.

EXAMPLE 36

Trans-5-(2-pyrrolidin-1-ylmethyl-cyclopentyl)-1H-indole-3-carbonitrile

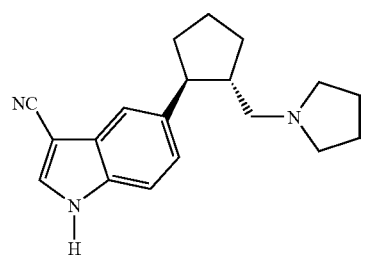

Trans-5-(2-pyrrolidin-1-ylmethyl-cyclopentyl)-1H-indole-3-carbonitrile was prepared (11%, 42%) by the method given in Example 31. LC-MS: 1.02 min (2 min gradient); 294.21 (MH)$^+$.

EXAMPLE 37

Trans-5-(ethylaminomethyl-cyclopentyl)-1H-indole-3-carbonitrile

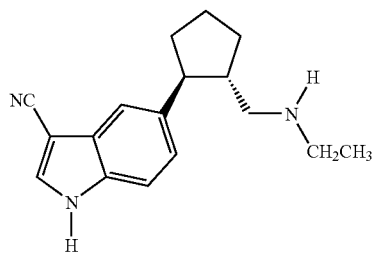

Trans-5-(ethylaminomethyl-cyclopentyl)-1H-indole-3-carbonitrile was prepared (5 mg, 21%) by the method given in Example 31. LC-MS: 1.02 min (2 min gradient); 268.16 (MH)$^+$.

EXAMPLE 38

Trans-5-{2-[(ethyl-methyl-amino)-methyl]-cyclopentyl}-1H-indole-3-carbonitrile

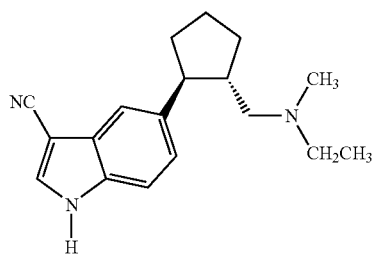

Trans-5-{2-[(ethyl-methyl-amino)-methyl]-cyclopentyl}-1H-indole-3-carbonitrile was prepared (8 mg, 33%) by the method given in Example 31. LC-MS: 1.03 min (2 min gradient); 282.21 (MH)$^+$.

EXAMPLE 39

Trans-5-(diethylaminomethyl-cyclopentyl)-1H-indole-3-carbonitrile

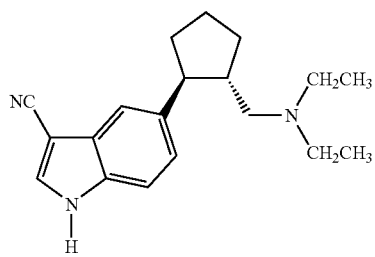

Trans-5-(diethylaminomethyl-cyclopentyl)-1H-indole-3-carbonitrile was prepared (7 mg, 28%) by the method given in Example 31. LC-MS: 1.05 min (2 min gradient); 296.21 (MH)$^+$.

EXAMPLE 40

Trans-5-{2-[(benzyl-methyl-amino)-methyl]-cyclopentyl}-1H-indole-3-carbonitrile

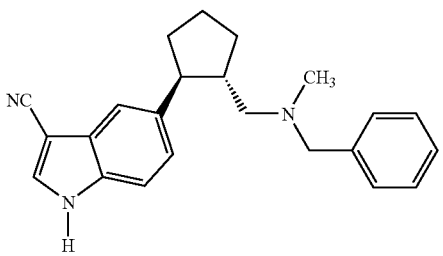

Trans-5-{2-[(benzyl-methyl-amino)-methyl]-cyclopentyl}-1H-indole-3-carbonitrile was prepared (9 mg, 33%) by the method given in Example 31. LC-MS: 1.20 min (2 min gradient); 344.17 (MH)$^+$.

EXAMPLE 41

Trans-5-(2-dimethylaminomethyl-cyclopentyl)-1-methyl-1H-indole-3-carbonitrile

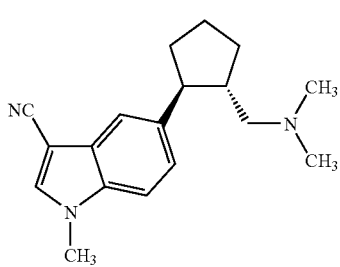

Trans-5-(2-dimethylaminomethyl-cyclopentyl)-1-methyl-1H-indole-3-carbonitrile was prepared (2 mg, 9%) from trans-5-(2-formyl-cyclopentyl)-1-methyl-1H-indole-3-carbonitrile by the method described in Example 31. LC-MS: 1.10 (2 min gradient); 282.20 (MH)$^+$.

EXAMPLE 42

Cis-5-(methylaminomethyl-cyclopentyl)-1H-indole-3-carbonitrile

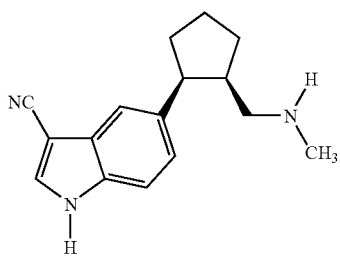

A solution of cis-5-(2-formyl-cyclopentyl)-1H-indole-3-carbonitrile (0.067 g, 0.28 mMol) in methanol (10 mL) was treated with methylamine (2M in tetrahydrofuran, 0.7 mL)

and sodium triacetoxyborohydride (0.30 g, 1.4 mMol). The solution was stirred at ambient temperature for 1 h, diluted with ethyl acetate, washed with 1M sodium hydroxide and brine, dried over sodium sulfate, and concentrated in vacuo. Silica gel flash column chromatography (10% 2M ammonia in methanol/chloroform) gave the product as a clear film (15 mg, 20%). $^1$H-NMR (500 MHz, CD$_3$OD) δ 7.96 (1H, d, J=5 Hz), 7.46 (2H, m), 7.19 (1H, m), 3.40 (1H, m), 2.39 (1H, m), 2.31–2.05 (5H, m), 1.98 (2H, m), 1.78 (1H, m), 1.60 (1H, m). LC-MS: 1.43 min (3 min gradient); 254.24 (MH)$^+$.

EXAMPLE 43

Cis-5-(dimethylaminomethyl-cyclopentyl)-1H-indole-3-carbonitrile

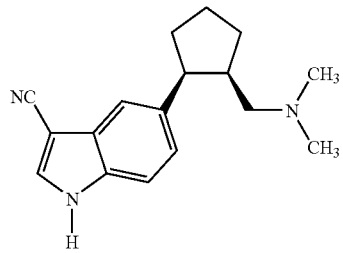

Cis-5-(dimethylaminomethyl-cyclopentyl)-1H-indole-3-carbonitrile was prepared (34 mg, 45%) by the method given in Example 39. $^1$H-NMR (500 MHz, CD$_3$OD) δ 7.90 (1H, m), 7.43 (2H, m), 7.17 (1H, m), 3.37 (1H, m), 2.39 (1H, m), 2.17–2.01 (7H, m), 1.97 (4H, m), 1.82 (2H, m), 1.67 (1H, m). LC-MS: 1.40 min (3 min gradient); 268.22 (MH)$^+$.

EXAMPLES 44 AND 45

Chiral HPLC Resolution of (+/−)-Trans-3-(2-dimethylaminomethyl-cyclopentyl)-1H-indole-5-carbonitrile (−)(1-R,2-R)-enantiomer (Example 44)

(+)(1-S,2-S)-enantiomer (Example 45)

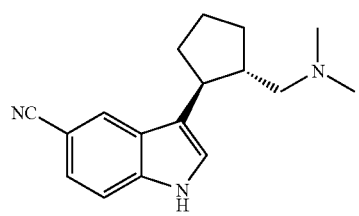

Racemic trans-3-(2-dimethylaminomethyl-cyclopentyl)-1H-indole-5-carbonitrile was dissolved in 2:1 hexanes/methanol and loaded on a Chiralpak AD column. The mixture was separated with an isocratic system of 5% solvent ethanol and 95% solvent B (0.05% diethylamine in hexanes). The (−)(1-R,2-R)-enantiomer (Example 44) eluted first {[α]$^{25}$-187.83 (589 nm, c 0.833 mg/mL, MeOH)}. The (+)(1-S,2-S)-enantiomer (Example 45) eluted second {[α]$^{25}$+138.5 (589 nm, c 0.833 mg/mL, MeOH)}.

EXAMPLES 46 AND 47

(+/−) trans-3-[2-(1-dimethylaminoethyl)cyclopentyl]-1H-indole-5-carbonitrile

Diastereomer A (Example 46)

Diastereomer B (Example 47)

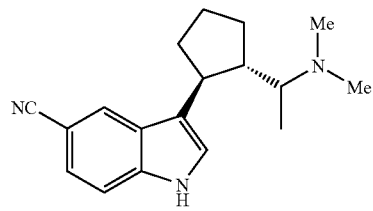

To a solution of (+/−) trans-3-(2-acetylcyclopentyl)-1H-indole-5-carbonitrile (72 mg, 0.29 mMol) in ethanol (10 mL) was added 4A molecular sieves (100 mg), acetic acid (17 uL, 0.29 mMol), dimethylamine (1.4 mL, 2M in THF, 2.9 mMol) and sodium cyanoborohydride (108 mg, 1.7 mMol). The reaction was heated at reflux for 2 days. The solvent was removed in vacuo and the residue was taken up in 1N sodium hydroxide, saturated with sodium chloride, and extracted with ethyl acetate (4×10 mL). The combined organic layers were dried with magnesium sulfate and the solvent removed in vacuo. The residue was purified on a Shimadzu reverse phase preparative HPLC with the following conditions: 20×100 mm S5 column, % B gradient from 30–60, gradient time 10 minutes. Mobile phase A was 10% methanol, 90% water, 0.1% trifluoroacetic acid. Mobile phase B was 90% methanol, 10% water, 0.1% trifluoroacetic acid.

EXAMPLE 46

Diastereomer A ( )

Eluting at 4.3 minutes was (+/−) trans-3-[2-(1-dimethylamino-ethyl)cyclopentyl]-1H-indole-5-carbonitrile diastereomer A, obtained as a TFA salt (17 mg, 15%): $^1$H NMR (400 MHz, CDCl$_3$) δ 8.54 (1H, brs), 7.92 (1H, s), 7.44 (2H, s), 7.25 (1H, m), 3.54 (1H, brs), 3.46 (1H, m, buried), 3.21 (1H, q, J=6.0 Hz), 2.75 (3H, d, J=4.8 Hz), 2.61 (3H, d, J=4.8 Hz), 2.60 (1H, buried), 1.62–2.30 (6H, m), 1.16 (3H, d, J=6.8 Hz); MS m/e 282.3 (M+H)$^+$.

EXAMPLE 47

Diastereomer B ( )

Eluting at 5.4 minutes was (+/−) trans-3-[2-(1-dimethylamino-ethyl)cyclopentyl]-1H-indole-5-carbonitrile diastereomer B, obtained as a TFA salt (18 mg, 16%): $^1$H NMR (400 MHz, CDCl$_3$) δ 8.88 (1H, brs), 7.88 (1H, s), 7.43 (3H, m), 4.54 (1H, brs), 3.41 (1H, m,), 2.98 (1H, q, J=6.0 Hz), 2.74 (3H, d, J=4.8 Hz), 2.55 (3H, d, J=4.8 Hz), 1.50–2.60 (7H, m), 1.31 (3H, d, J=7.1 Hz); MS m/e 282.3 (M+H)$^+$.

EXAMPLE 48 AND 49

Chiral HPLC Resolution of Example 46

Diastereomer A of (+/−) trans-3-[2-(1-dimethylaminoethyl)cyclopentyl]-1H-indole-5-carbonitrile, Enantiomer A: Example 48 ( )

Enantiomer B: Example 49 ( )

A sample of 19 mg of racemic (+/−) trans-3-[2-(1-dimethylaminoethyl)cyclopentyl]-1H-indole-5-carbonitrile diastereomer A was separated into separate enantiomers by chiral HPLC. The column was 10 um Chiralpack AD, 4.6 mm×250 mm. The mobile phase was an isocratic system composed of 5% ethanol and 95% hexanes containing 0.05% diethylamine, and the flow rate was 9.0 mL/min.

EXAMPLE 48

Enantiomer A ( )

At 9.7 minutes enantiomer A was eluted, yielding 4.7 mg after evaporation.

EXAMPLE 49

Enantiomer B ( )

At 12.7 minutes enantiomer B was eluted, yielding 5.4 mg after evaporation.

EXAMPLE 50 AND 51

(+/−) trans-3-[2-(1-dimethylaminopropyl)cyclopentyl]-1H-indole-5-carbonitrile

Diastereomer A: Example 50 ( )

Diastereomer B: Example 51 ( )

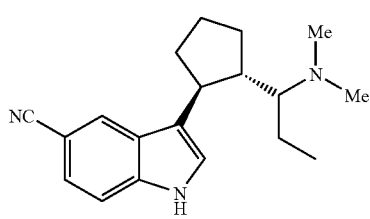

A solution of (+/−) trans-3-(2-propionylcyclopentyl)-1H-indole-5-carbonitrile (40 mg, 0.15 mMol), dimethylamine (0.19 mL, 2M in THF, 0.38 mMol), and titanium(IV)isopropoxide (64 mg, 0.23 mMol) in ethanol (3 mL) was stirred for 2 hours at room temperature. Sodium borohydride (6 mg, 0.15 mMol) was added and the reaction was stirred a further 2 days. The reaction was filtered through celite, the solvent was removed in vacuo and the residue was taken up in 1N sodium hydroxide (5 mL), saturated with sodium chloride, and extracted with ethyl acetate (3×5 mL). The combined organic layers were dried with magnesium sulfate and the solvent removed in vacuo. The residue was purified on a Shimadzu reverse phase preparative HPLC with the following conditions: 20×100 mm S5 column, % B gradient from 30–60, gradient time 10 minutes. Mobile phase A was 10% methanol, 90% water, 0.1% trifluoroacetic acid. Mobile phase B was 90% methanol, 10% water, 0.1% trifluoroacetic acid.

EXAMPLE 50

Diastereomer A ( )

Eluting at 4.3 minutes was (+/−) trans-3-[2-(1-dimethylamino-propyl)cyclopentyl]-1H-indole-5-carbonitrile diastereomer A, obtained as a TFA salt (5 mg, 11%): $^1$H NMR (400 MHz, CDCl$_3$) δ 8.70 (1H, brs), 7.92 (1H, s), 7.44 (2H, s), 7.37 (1H, m), 3.40 (1H, q, J=7.5 Hz), 3.11 (1H, m), 2.69 (3H, d, J=4.3 Hz), 2.63 (3H, d, J=4.4 Hz), 2.70 (1H, buried), 1.55–2.40 (8H, m), 0.98 (3H, t, J=7.5 Hz); MS m/e 296.2 (M+H)$^+$.

EXAMPLE 51

Diastereomer B ( )

Eluting at 5.4 minutes was was (+/−) trans-3-[2-(1-dimethylaminopropyl)-cyclopentyl]-1H-indole-5-carbonitrile diasteromer B, obtained as a TFA salt (3 mg, 7%): $^1$H NMR (400 MHz, CDCl$_3$) δ 8.67 (1H, brs), 7.90 (1H, s), 7.43 (3H, m), 3.12 (1H, m,), 3.01 (1H, q, J=7.9 Hz), 2.69 (3H, d, J=4.2 Hz), 2.64 (1H, buried), 2.47 (3H, d, J=3.8 Hz), 1.65–2.25 (8H, m), 1.12 (3H, t, J=7.6 Hz); MS m/e 296.2 (M+H)$^+$.

EXAMPLE 52

(1S,2S)-[2-(5-iodo-1H-indol-3-yl)-cyclopentylmethyl]-dimethylamine

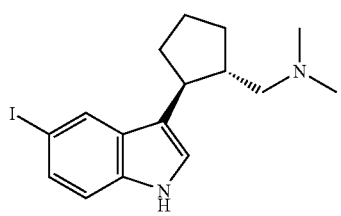

To a room temperature solution of (1S,2S)-2-(5-iodo-1H-indol-3-yl)-cyclo-pentanecarbaldehyde (17.5 g, 51.6 mMol) in 200 mL of methanol was added with stirring dimethylamine (64 mL of a 2.0 M solution in THF, 128 mMol) followed by acetic acid (0.5 mL). After 15 min, NaBH (OAc)$_3$ (12 g, 57 mMol) was added slowly. The resulting mixture was stirred 18 h and was then concentrated under vacuum. The residue was partitioned between ethyl acetate (400 mL) and aqueous NaHCO$_3$ (300 mL). The organic layer was washed twice with aqueous NaHCO$_3$ (250 mL). Every aqueous layer was extracted with ethyl acetate (50 mL) to make sure no product was left in aqueous. The combined organic extracts were then dried over MgSO$_4$. Solvent was removed under vacuum and the residue was pump dried overnight to give crude trans [2-(5-iodo-1H-indol-3-yl)-cyclopentylmethyl]-dimethylamine (19.4 g, 100%) which was used directly for the next reaction without further purification. An analytical sample was prepared by crystallization from ethyl acetate. $^1$H NMR (400 MHz, methanol-d$_4$) δ 7.86 (s, 1H), 7.30 (d, 1H), 7.14 (d, 1H), 7.02 (s, 1H), 2.80 (m, 1H), 2.27 (m, 3H), 2.12 (s, 6H), 2.10 (m, 2H), 1.79 (m, 3H), 1.46 (m, 1H); $^{13}$C NMR (400 MHz, methanol-d$_4$), δ 137.6, 131.1, 130.5, 128.9, 123.2, 119.0, 114.6, 82.3, 66.2, 46.0, 45.6, 43.4, 35.0, 33.0, 25.2; HRMS (EI), exact mass calc'd for C$_{16}$H$_{21}$IN$_2$ (M+H) 369.0828, found 369.0836.

EXAMPLE 53

Alternate Procedure for the Preparation of (1S,2S)-3-(2-dimethylaminomethyl-cyclopentyl)-1H-indol-5-carbonitrile Which is Described as Example 45 ( )

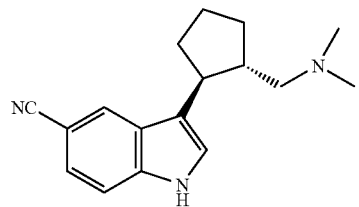

N,N'-dimethylethylenediamine (5.66 mL, 53 mMol) was added to a mixture of trans [2-(5-iodo-1H-indol-3-yl)-cyclopentylmethyl]-dimethylamine (19.4 g, 53 mMol), sodium cyanide (3.1 g, 63 mMol), and copper(I) iodide (1 g, 5.3 mMol) in deoxygenated anhydrous toluene (50 mL). The resulting mixture was heated in an oil bath to 125° C. under N$_2$ for ~18 h. The reaction was cooled to 50° C., diluted with ethyl acetate (400 mL), and heated to reflux for 5 min. The resulting suspension was transferred to a separatory funnel and washed with aqueous NaHCO$_3$ (400 mL and twice with 200 mL). Every aqueous layer was extracted with ethyl acetate (50 mL) to make sure no product was left in aqueous layer. The combined organic layers were dried over MgSO$_4$. Solvent was removed in vacuo to give the crude product which was purified by silica gel chromatography using dichloromethane/2.0 M ammonia in methanol (100/0 to 93/7) as the eluent, to give trans 3-(2-dimethylaminomethyl-cyclopentyl)-1H-indole-5-carbonitrile (11.7 g, 83%).

3-(2-Dimethylaminomethyl-cyclopentyl)-1H-indole-5-carbonitrile (11.7 g, 44 mMol) was dissolved in a mixture of methanol (10 mL) and methylene chloride (50 mL) and treated with HCl/ether (22 mL, 2.0 M) at RT. After stirring for 30 min, the solvent was removed in vacuo and the residue was sonicated in methanol (~20 mL), cooled, and then filtered to give a white solid which was recrystallized from ethanol to give white crystals (7.3 g, 55%). $^1$H NMR (400 MHz, methanol-d$_4$) δ 8.04 (s, 1H), 7.48 (d, 1H), 7.36 (dd, 2H), 3.15 (t, 1H), 3.04 (m, 2H), 2.78 (s, 6H) 2.55 (m, 1H), 2.21 (m, 2H), 1.89 (m, 3H), 1.56 (m, 1H); $^{13}$C NMR (400 MHz, methanol-d$_4$), δ 140.4, 128.0, 125.6, 125.5, 125.4, 122.0, 118.7, 113.8, 102.5, 63.8, 44.0, 43.6, 43.1, 35.0, 31.7, 24.9. HRMS (EI), exact mass calc'd for C$_{17}$H$_{21}$N$_3$ (M+H) 268.1814, found 268.1811. Anal. Calcd. for C$_{17}$H$_{21}$N$_3$·HCl: C, 67.20; H, 7.29; N, 13.83; Cl, 11.66.

Found: C, 67.03; H, 7.50; N, 13.78; Cl, 11.53. Chiral HPLC (Chirapak AD column, 4.6×250 mm, 101 μm, 5% ethanol/95% hexane containing 0.15% DEA, flow rate 1.0 mL/min). Retention time: 13.54 min, 100% ee, [α]$^{20}$$_D$=55.18° (c=2.8, methanol). Absolute configuration (S, S) was confirmed by single crystal X-ray analysis.

EXAMPLE 54

3-(2-Dimethylamino-cyclopentylmethyl)-1H-indole-5-carbonitrile

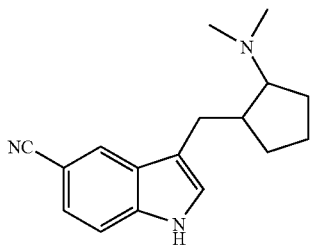

A solution of 3-(2-oxo-cyclopentylmethyl)-1H-indole-5-carbonitrile (45 mg, 0.19 mMol), dimethylamine (1.92 mL, 3.78 mMol, 2.0 M/THF), sodium cyanoborohydride (0.12 g, 1.9 mMol) and acetic acid (0.2 mL) in ethanol (10 mL) was stirred for 16 h. The solution was cooled in an ice-bath and quenched with aqueous hydrochloric acid (2 mL, 1 N). The mixture was stirred for 5 min and then poured into a saturated aqueous solution of sodium bicarbonate (15 mL) and brine (10 mL). The aqueous layer was extracted with ethyl acetate (3×50 mL). The combined organic extracts were washed with brine (20 mL), dried over anhydrous sodium sulfate, and concentrated in vacuo. The crude material was purified by silica gel column chromatography using a step gradient of 0.5% MeOH/CHCl$_3$-30% MeOH/CHCl$_3$ to give 3-(2-dimethylamino-cyclopentylmethyl)-1H-indole-5-carbonitrile (13.0 mg, 26%) as a mixture of diastereomers. $^1$H NMR (400 MHz, DMSO-d$_6$) δ 7.98 (1H, s), 7.50 (1H, d, J=8.4 Hz), 7.38 (2H, m), 2.89 (1H, m), 2.33 (9H, m), 1.82 (2H, m), 1.57 (2H, m), 1.42 (2H, m); LCMS (Method A:

4.6×50 mm XTERRA C-18 S5 column, 5 mL/min, 0–100% MeOH/H₂O/0.1% TFA, 2 min gradient): T$_r$=1.09 min, m/e 268 (M+H)⁺.

EXAMPLE 55

3-(2-Methylamino-cyclopentylmethyl)-1H-indole-5-carbonitrile

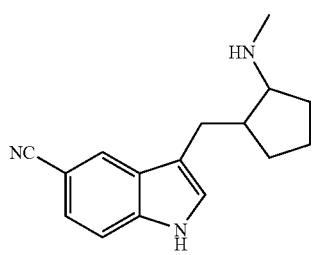

This compound was synthesized in the same manner as described above Example 54. The crude product was purified by preparative HPLC to give 3-(2-methylamino-cyclopentylmethyl)-1H-indole-5-carbonitrile as a TFA salt (2.3 mg, 5%). LCMS (Method A) ret. time 0.96 min, m/e 254 (M+H)⁺.

EXAMPLE 56

3-(2-Ethylamino-cyclopentylmethyl)-1H-indole-5-carbonitrile

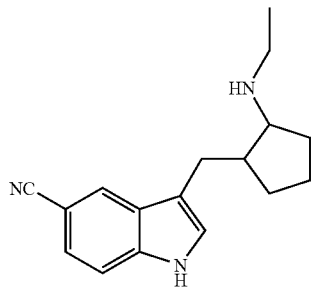

This compound was synthesized in the same manner as described above Example 54. The crude product was purified by preparative HPLC to give 3-(2-ethylamino-cyclopentylmethyl)-1H-indole-5-carbonitrile as a TFA salt (104 mg, 43%). ¹H NMR (400 MHz, DMSO-D₆) δ 1.19 (t, J=7.21 Hz, 3H) 1.51 (m, 6H) 2.04 (m, 1H) 2.29 (m, 1H) 2.92 (m, 2H) 3.06 (m, 2H) 7.42 (m, 2H) 7.52 (m, 1H) 8.17 (dd, J=12.23, 1.47 Hz, 1H) 8.40 (m, 2H); LCMS (Method A) ret. time 0.96 min, m/e 268 (M+H)⁺.

EXAMPLE 57

3-(2-Diethylamino-cyclopentylmethyl)-1H-indole-5-carbonitrile

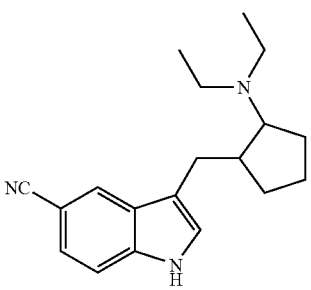

This compound was synthesized in the same manner as described above Example 54. The crude product was purified by preparative HPLC to give 3-(2-diethylamino-cyclopentylmethyl)-1H-indole-5-carbonitrile was gave as a TFA salt (34 mg, 13%). LCMS (Method A) ret. time 0.92 min, m/e 296 (M+H)⁺.

EXAMPLE 58

3-[2-(Ethyl-methyl-amino)-cyclopentylmethyl]-1H-indole-5-carbonitrile

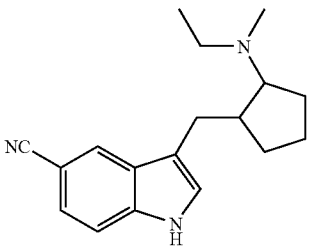

This compound was synthesized in the same manner as described above Example 54. The crude product was purified by preparative HPLC to give 3-[2-(ethyl-methyl-amino)-cyclopentylmethyl]-1H-indole-5-carbonitrile as a TFA salt (152 mg, 61%). ¹H NMR (400 MHz, DMSO-D6) δ 1.31 (m, 7H) 2.00 (m, 3H) 2.63 (m, 4H) 3.18 (m, 4H) 7.47 (m, 3H) 8.11 (s, 1H) 9.13 (m, 1H); LCMS (Method A) ret. time 0.87 min, m/e 282 (M+H)⁺.

EXAMPLE 59

3-(2-Pyrrolidin-1-yl-cyclopentylmethyl)-1H-indole-5-carbonitrile

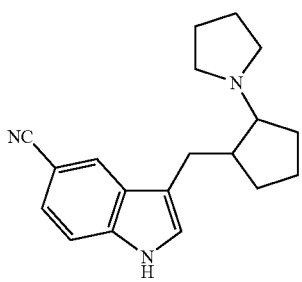

This compound was synthesized in the same manner as described above Example 54. The crude product was purified by preparative HPLC to give 3-(2-pyrrolidin-1-yl-cyclopentylmethyl)-1H-indole-5-carbonitrile as a TFA salt (81 mg, 32%). $^1$H NMR (400 MHz, DMSO-D$_6$) δ 1.41 (m, 2H) 1.59 (m, 1H) 2.01 (m, 6H) 2.52 (m, 3H) 2.84 (d, J=12.96 Hz, 1H) 3.17 (m, 1H) 3.34 (m, 1H) 3.59 (m, 2H) 3.94 (m, 1H) 7.46 (m, 3H) 8.11 (s, 1H) 9.49 (br s, 1H); LCMS (Method A) ret. time 0.89 min, m/e 294 (M+H)$^+$.

EXAMPLE 60

3-[2-(Benzyl-methyl-amino)-cyclopentylmethyl]-1H-indole-5-carbonitrile

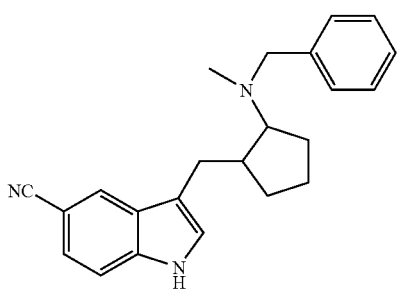

This compound was synthesized in the same manner as described above Example 54. The crude product was purified by preparative HPLC to give 3-[2-(benzyl-methyl-amino)-cyclopentylmethyl]-1H-indole-5-carbonitrile as a TFA salt (202 mg, 70%). LCMS (Method A) ret. time 1.13 min, m/e 344 (M+H)$^+$.

Serotonin Transporter Binding Assay

HEK-293 cells that stably express human serotonin transporters (HEK-hSERT cells) were grown at 37° C. in 5% CO$_2$ as a monolayer in medium consisting of EMEM supplemented with 10% fetal bovine serum and G418 sulfate (500 μg/mL). To prepare membranes for radioligand binding experiments, cells were rinsed twice with phosphate-buffered saline (138 mM NaCl, 4.1 mM KCl, 5.1 mM Na$_2$PO$_4$, 1.5 mM KH$_2$O$_4$, 11.1 mM glucose, pH 7.4). Cells were transferred from plates to polypropylene tubes (16×100 mm), centrifuged at 1,200×g for 5 min and were frozen at −80° C. until assay. Following centrifugation, pellets were resuspended by homogenization in buffer consisting of 50 mM Tris (pH 7.7 at 25° C.), 120 mM NaCl and 5 mM KCl and then centrifuged at 32,000×g for 10 min. Following centrifugation, supernatants were discarded and pellets were resuspended in buffer consisting of 50 mM Tris (pH 7.4 at 25° C.), 150 mM NaCl and 5 mM KCl. Membrane homogenates (200 μl/plate) were incubated with 1 nM [$^3$H]-citalopram (specific activity=85 Ci/mMol) and increasing concentrations of test compounds for 1 hr at 25° C. in a total volume of 250 μl. The assay buffer consisted of 50 mM Tris (pH 7.4 at 25° C.), 120 mM NaCl and 5 mM KCl (pH 7.4 with conc. HCl). Plates were incubated for 1 hr at 25° C., then filtered through 0.5% PEI treated Whatman GF/B filters using a Brandel cell harvester. Filters were washed three times with 3 mL of ice-cold tris wash buffer. Non-specific binding was defined with 10 μM fluoxetine. Amount of radioligand bound in the presence and absence of competitor was analyzed by plotting (−)log drug concentration versus the amount of radioligand specifically bound. The midpoint of the displacement curve (IC$_{50}$, nM), signifies the potency. K$_i$ values were calculated using the method of Cheng and Prusoff (1973).

Norepinephrine Transporter Binding Assay

MDCK cells that stably express human norepinephrine transporters (HEK-hNET cells) were supplied by Receptor Biology, Inc. Pellets were resuspended by homogenization in buffer consisting of 50 mM Tris (pH 7.4 at 25° C.), 120 mM NaCl and 5 mM KCl. Membrane homogenates (200 μl/well, 8 ug protein) were incubated with 2.7 nM [$^3$H]-nisoxetine (specific activity=80 Ci/mMol) and increasing concentrations of test compounds for 1 hr at 4° C. in a total volume of 250 μl. The assay buffer consisted of 50 mM Tris (pH 7.4 at 25° C.), 120 mM NaCl and 5 mM KCl (pH 7.4 with conc. HCl). Plates were incubated for 1 hr at 4° C., then filtered through 0.5% PEI treated Whatman GF/B filters using a Brandel cell harvester. Filters were washed three times with 3 mL of ice-cold tris wash buffer. Non-specific binding was defined with 10 μM desipramine. Amount of radioligand bound in the presence and absence of competitor was analyzed by plotting (−)log drug concentration versus the amount of radioligand specifically bound. The midpoint of the displacement curve ($IC_{50}$, nM), signifies the potency. $K_i$ values were calculated using the method of Cheng and Prusoff (1973).

Compounds of the present invention demonstrate SERT binding and may be useful for the treatment of depression, anxiety disorders, premature ejaculation, chronic pain, obsessive-compulsive disorder, feeding disorders, premenstrual dysphoric disorder and panic disorders. Moreover, particular compounds of Formula (I) demonstrate no norepinephrine reuptake inhibition, and therefore should have a reduced probability of any cardiovascular liabilities associated with norepinephrine reuptake inhibition.

In the Table 1 below, binding results are denoted as follows:
A: $K_i < 1$ nM;
B: $1$ nM $< K_i < 10$ nM;
C: $10$ nM $< K_i < 100$ nM;
D: $100$ nM $< K_i < 500$ nM;
E: $500$ nM $< K_i < 1000$ nM;
F: $K_i > 1000$ nM

TABLE 1

5-HT and NE reuptake data for Compounds of Formula 1.

| EXAMPLE | STRUCTURE | NAME | 5-HT reuptake binding Ki (nM) | NE reuptake binding Ki (nM) |
|---|---|---|---|---|
| 25 | 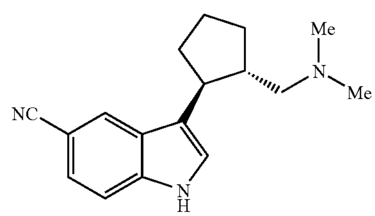 | Trans-3-(2-Dimethylaminomethyl-cyclopentyl)-1H-indole-5-carbonitrile | A | F |
| 26 | 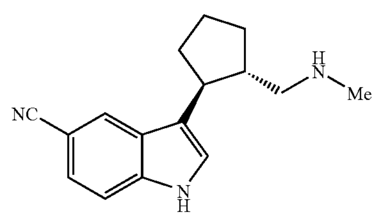 | Trans-3-(2-Methylaminomethyl-cyclopentyl)-1H-indole-5-carbonitrile | B | F |
| 27 | 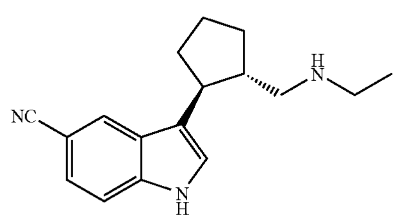 | Trans-3-(2-Ethylaminomethyl-cyclopentyl)-1H-indole-5-carbonitrile | C | F |
| 28 | 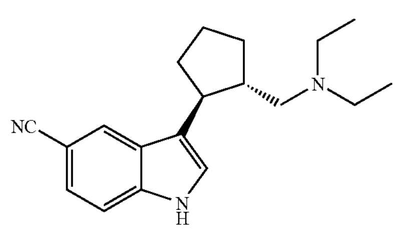 | Trans-3-(2-Diethylaminomethyl-cyclopentyl)-1H-indole-5-carbonitrile | D | F |
| 29 | 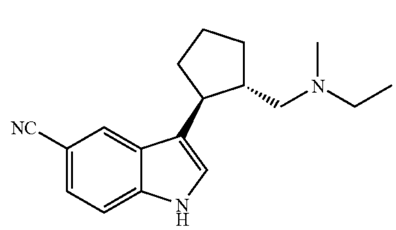 | Trans-3-{2-[(Ethyl-methyl-amino)-methyl]-cyclopentyl}-1H-indole-5-carbonitrile | B | F |

TABLE 1-continued

5-HT and NE reuptake data for Compounds of Formula 1.

| EXAMPLE | STRUCTURE | NAME | 5-HT reuptake binding Ki (nM) | NE reuptake binding Ki (nM) |
|---|---|---|---|---|
| 30 | 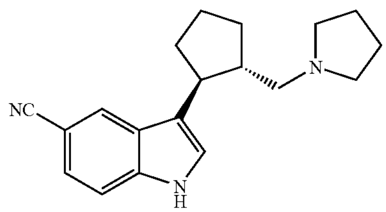 | Trans-3-(2-Pyrrolindin-1-ylmethyl-cyclopentyl)-1H-indole-5-carbonitrile | B | F |
| 31 | 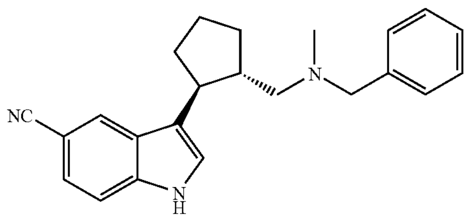 | Trans-3-{2-[(Benzyl-methyl-amino)-methyl]-cyclopentyl}-1H-indole-5-carbonitrile | C | F |
| 32 | 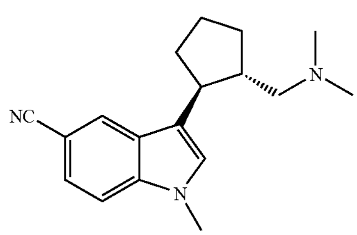 | Trans-3-(2-Dimethylaminomethyl-cyclopentyl)-1-methyl-1H-indole-5-carbonitrile | B | F |
| 33 | 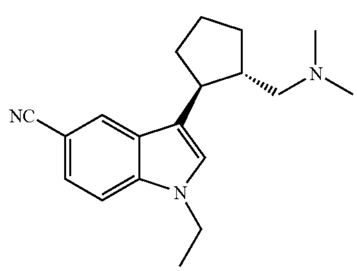 | Trans-3-(2-Dimethylaminomethyl-cyclopentyl)-1-ethyl-1H-indole-5-carbonitrile | B | F |
| 34 | 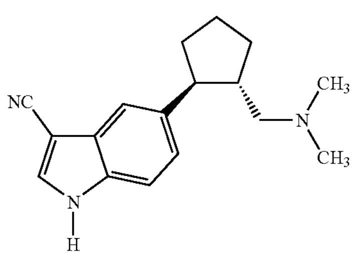 | Trans-5-(2-Dimethylaminomethyl-cyclopentyl)-1H-indole-3-carbonitrile | B | F |
| 35 | 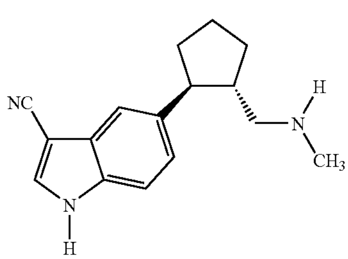 | Trans-5-(2-Methylaminomethyl-cyclopentyl)-1H-indole-3-carbonitrile | B | F |

TABLE 1-continued

5-HT and NE reuptake data for Compounds of Formula 1.

| EXAMPLE | STRUCTURE | NAME | 5-HT reuptake binding Ki (nM) | NE reuptake binding Ki (nM) |
|---|---|---|---|---|
| 36 | 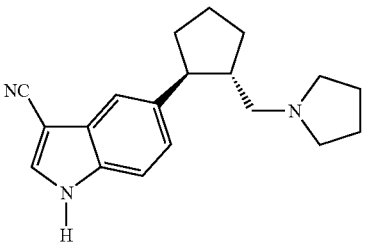 | Trans-5-(2-Pyrrolidin-1-ylmethyl-cyclopentyl)-1H-indole-3-carbonitrile | D | F |
| 37 | 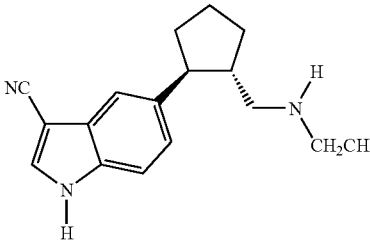 | Trans-5-(2-Ethylaminomethyl-cyclopentyl)-1H-indole-3-carbonitrile | D | F |
| 38 | 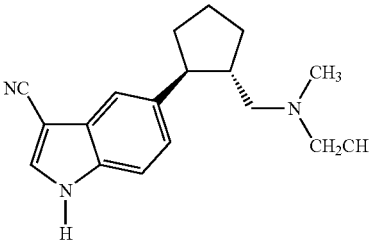 | Trans-5-{2-[(Ethyl-methyl-amino)-methyl]-cyclopentyl}-1H-indole-3-carbonitrile | D | F |
| 39 | 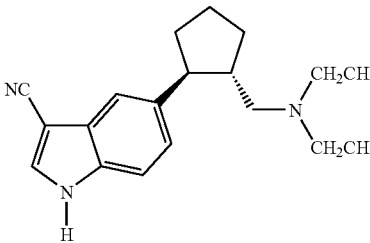 | Trans-5-(2-Diethylaminomethyl-cyclopentyl)-1H-indole-3-carbonitrile | D | F |
| 40 | 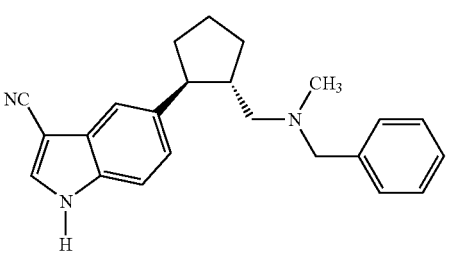 | Trans-5-{2-[(Benzyl-methyl-amino)-methyl]-cyclopentyl}-1H-indole-3-carbonitrile | C | F |

TABLE 1-continued

5-HT and NE reuptake data for Compounds of Formula 1.

| EXAMPLE | NAME | 5-HT reuptake binding Ki (nM) | NE reuptake binding Ki (nM) |
|---|---|---|---|
| 41 | Trans-5-(2-dimethylaminomethyl-cyclopentyl)-1-methyl-1H-indole-3-carbonitrile | D | F |
| 42 | cis-5-(2-Methylaminomethyl-cyclopentyl)-1H-indole-3-carbonitrile | C | D |
| 43 | cis-5-(2-dimethylaminomethyl-cyclopentyl)-1H-indole-3-carbonitrile | B | NOT TESTED |
| 44 | (1R, 2R)-3-(2-Dimethylaminomethyl-cyclopentyl)-1H-indole-5-carbonitrile (enantiomer A) | C | F |
| 45 | (1S, 2S)-3-(2-Dimethylaminomethyl-cyclopentyl)-1H-indole-5-carbonitrile (enantiomer B) | A | F |
| 46 | (+/−) trans-3-[2-(1-dimethylaminoethyl)cyclopentyl]-1H-indole-5-carbonitrile, diastereomer A | A | F |

TABLE 1-continued

5-HT and NE reuptake data for Compounds of Formula 1.

| EXAMPLE | STRUCTURE | NAME | 5-HT reuptake binding Ki (nM) | NE reuptake binding Ki (nM) |
|---|---|---|---|---|
| 47 | 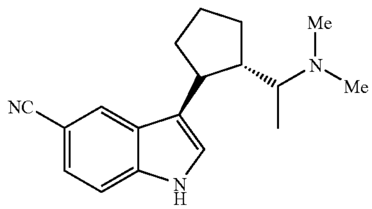 | (+/−) trans-3-[2-(1-dimethylaminoethyl)cyclopentyl]-1H-indole-5-carbonitrile, diastereomer B | B | NOT TESTED |
| 48 | 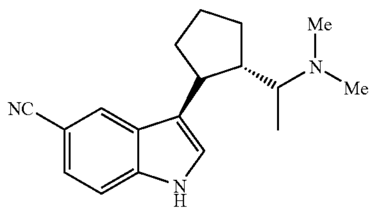 | Enantiomer A of Example 46 | C | NOT TESTED |
| 49 | 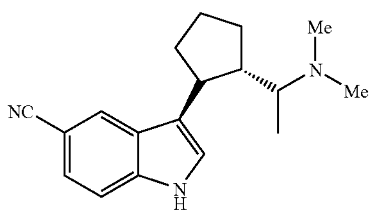 | Enantiomer B of Example 46 | A | NOT TESTED |
| 50 | 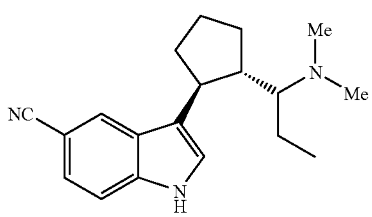 | (+/−) trans-3-[2-(1-dimethylaminopropyl)cyclopentyl]-1H-indole-5-carbonitrile, diastereomer A | C | NOT TESTED |
| 51 | 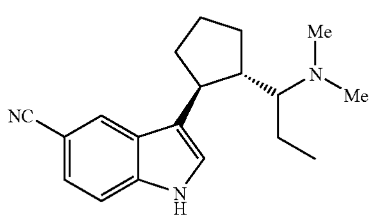 | (+/−) trans-3-[2-(1-dimethylaminopropyl)cyclopentyl]-1H-indole-5-carbonitrile, diastereomer B | D | NOT TESTED |
| 52 | 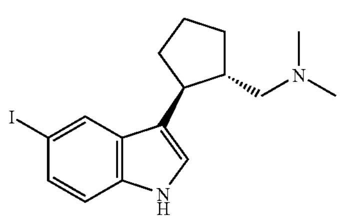 | (1S, 2S)-[2-(5-iodo-1H-indol-3-yl)-cyclopentylmethyl]-dimethylamine | C | NOT TESTED |

TABLE 1-continued

5-HT and NE reuptake data for Compounds of Formula 1.

| EXAMPLE | STRUCTURE | NAME | 5-HT reuptake binding Ki (nM) | NE reuptake binding Ki (nM) |
|---|---|---|---|---|
| 54 | 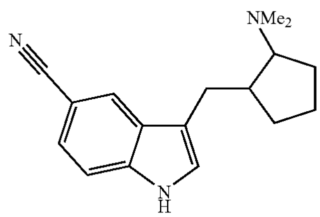 | 3-(2-Dimethylamino-cyclopentylmethyl)-1H-indole-5-carbonitrile | B | NOT TESTED |
| 55 | 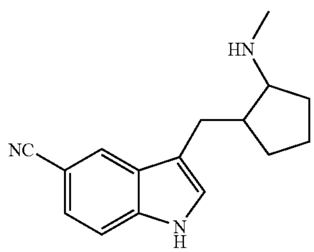 | 3-(2-Methylamino-cyclopentylmethyl)-1H-indole-5-carbonitrile | B | NOT TESTED |
| 56 | 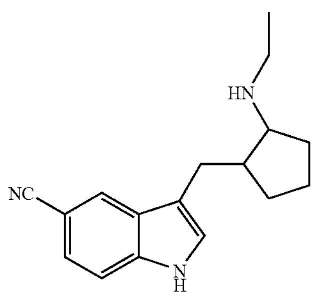 | 3-(2-Ethylamino-cyclopentylmethyl)-1H-indole-5-carbonitrile | B | NOT TESTED |
| 57 | 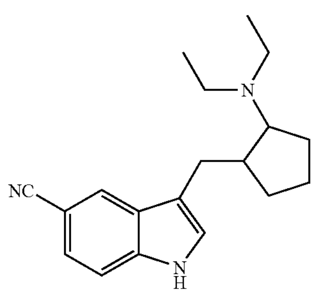 | 3-(2-Diethylamino-cyclopentylmethyl)-1H-indole-5-carbonitrile | C | NOT TESTED |
| 58 | 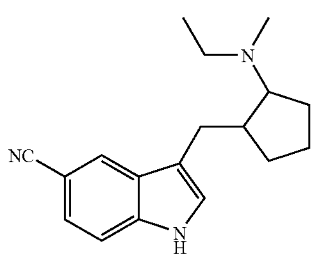 | 3-[2-(Ethyl-methyl-amino)-cyclopentylmethyl]-1H-indole-5-carbonitrile | B | NOT TESTED |

TABLE 1-continued

5-HT and NE reuptake data for Compounds of Formula 1.

| EXAMPLE | STRUCTURE | NAME | 5-HT reuptake binding Ki (nM) | NE reuptake binding Ki (nM) |
|---|---|---|---|---|
| 59 | 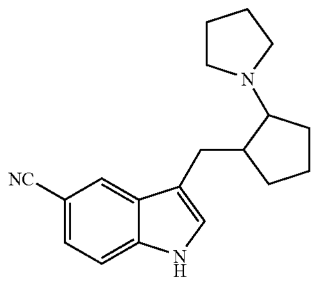 | 3-(2-Pyrrolidin-1-yl-cyclopentylmethyl)-1H-indole-5-carbonitrile | B | NOT TESTED |
| 60 | 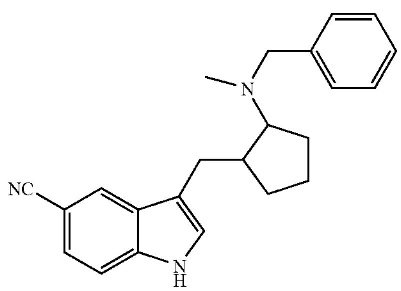 | 3-[2-(Benzyl-methyl-amino)-cyclopentylmethyl]-1H-indole-5-carbonitrile | C | NOT TESTED |

What is claimed is:

1. A compound of Formula (I)

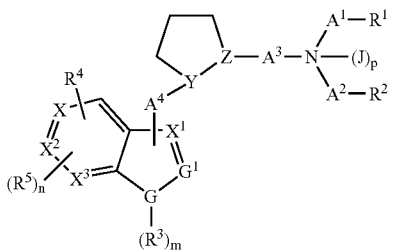

or a pharmaceutically acceptable salt or solvate thereof wherein $A^1$ and $A^2$ are each independently $C_{1-4}$alkylene or a bond;

$A^3$ is a bond, $C_{1-4}$alkylene or $C_{1-4}$alkylidene;

$A^4$ is $C_{1-4}$alkylene or a bond and is attached to X, $X^1$ or $X^2$;

X, $X^1$, $X^2$ and $X^3$ are independently C or CH;

J is $C_{1-4}$alkyl;

p is 0 or 1;

$R^1$ and $R^2$ are independently H, $C_{1-3}$alkyl, $C_{3-6}$cycloalkyl, phenyl, —O-phenyl, —N(H)C(O)O—$C_{1-4}$alkyl or $C_{1-4}$alkyl-N(H)C(O)O—;

said $C_{3-6}$cycloalkyl, phenyl or O-phenyl being independently and optionally substituted with $C_{1-4}$alkyl, $C_{1-3}$alkoxy, indolyl or halo;

wherein said indolyl is optionally substituted by halo or cyano;

or are independently selected from the group of heterocyclic moieties consisting of thienyl, furanyl, pyrrolyl, pyrrolinyl, pyrrolidinyl, imidazolyl, imidazolinyl, imidazolidinyl, pyrazolyl, pyrazolinyl pyrazolidinyl, pyridyl, pyrimidinyl, piperidinyl, piperazinyl, morpholino, adamantyl, indolyl, isoindolyl, indolinyl, quinolinyl, dihydroquinolinyl, tetrahydroquinolinyl, isoquinolinyl, dihydroisoquinolinyl and tetrahydroisoquinolinyl, wherein said heterocyclic moieties are optionally substituted with halo, $C_{1-4}$alkyl, $C_{1-4}$alkoxy or cyano;

or wherein -$A^1$-$R^1$ and -$A^2$-$R^2$ together with the nitrogen to which they are attached form pyrrolidinyl, piperidinyl, piperazinyl, morpholino, dihydroquinolinyl, tetrahydroquinolinyl, dihydroisoquinolinyl or tetrahydroisoquinolinyl and are optionally substituted with halo, $C_{1-4}$alkyl, $C_{1-4}$alkoxy, cyano or benzyl;

$R^3$ is H or $C_{1-4}$alkyl;

m is 0 or 1;

$R^4$ and $R^5$ are independently hydrogen, cyano, halo, nitro, $C_{1-3}$alkyl or $C_{1-3}$perfluoroalkyl;

wherein said $R^4$ or $R^5$ may be independently attached to $G^1$, X, $X^1$, $X^2$ or $X^3$;

n is 0 or 1;

G is N, O or S;

$C^1$ is N, C or CH;

Y is (D)H wherein D is C; and

Z is (E)H wherein E is C;

provided that both $R^4$ and $R^5$ are not attached to the same of said $C^1$, X, $X^1$, $X^2$ or $X^3$;

if G is O or S, then m is 0;

if G is N, then m is 1;

if $R_1$ is $C_{3-6}$cycloalkyl, phenyl or O-phenyl being independently and optionally substituted with $C_{1-4}$alkyl, $C_{1-3}$alkoxy, indolyl or halo; wherein said indolyl is optionally substituted by halo or cyano, then $R_2$ is H or $C_{1-3}$alkyl;

if $R^2$ is $C_{1-4}$cycloalkyl, phenyl or O-phenyl being independently and optionally substituted with $C_{1-4}$alkyl, $C_{1-3}$alkoxy, indolyl or halo;

wherein said indolyl is optionally substituted by halo or cyano, then $R_1$ is H or $C_{1-3}$alkyl;

if -$A^1$-$R^1$ and -$A^2$-$R^2$ together with the nitrogen to which they are attached form pyrrolidinyl, piperidinyl, piperazinyl, morpholino, dihydroquinolinyl, tetrahydroquinolinyl, dihydroisoquinolinyl or tetrahydroisoquinolinyl and are optionally substituted with halo, $C_{1-4}$alkyl, $C_{1-4}$alkoxy, cyano or benzyl, then p is 0;

if $R^1$ is —N(H)C(O)O$C_{1-4}$alkyl, $C_{1-4}$alkyl-N(H)C(O)O— or said heterocylic moiety wherein said heterocyclic moiety contains a nitrogen atom and said nitrogen atom is attached to $A^1$, then $A^1$ is $C_{2-4}$alkylene;

if $R^2$ is —N(H)C(O)O$C_{1-4}$alkyl, $C_{1-4}$alkyl-N(HH)C(O)O— or said heterocylic moiety wherein said heterocyclic moiety contains a nitrogen atom and said nitrogen atom is attached to $A^2$, then $A^2$ is $C_{2-4}$alkylene;

if $R^1$ is N(H)C(O)O—$C_{1-4}$alkyl, $C_{1-4}$alkyl-N(H)C(O)O— or a heterocyclic moiety selected from the group consisting of thienyl, furanyl, pyrrolyl, pyrrolinyl, pyrrolidinyl, imidazolyl, imidazolinyl, imidazoildinyl, pyrazolyl, pyrazolinyl, pyrazolidinyl, pyridyl, pyrimidinyl, piperidinyl, piperazinyl, morpholino, adamantyl, indolyl, isoindolyl, indolinyl, quinolinyl, dihydroquinolinyl, tetrahydroquinolinyl, isoquinolinyl, dihydroisoquinolinyl and tetrahydroisoquinolinyl, wherein said heterocyclic moieties are optionally substituted with halo, $C_{1-4}$alkyl, $C_{1-4}$alkoxy or cyano, then $R^2$ is H or $C_{1-3}$alkyl;

if $R^2$ is —N(H)C(O)O—$C_{1-4}$alkyl, $C_{1-4}$alkyl-N(H)C(O)O— or a heterocyclic moiety selected from the group consisting of thienyl, furanyl, pyrrolyl, pyrralinyl, pyrrolidinyl, imnidazolyl, imidazolinyl, imidazolidinyl, pyrazolyl, pyrazolinyl, pyrazolidinyl, pyridyl, pyrimidinyl, piperidinyl, piperazinyl, morpholino, adamantyl, indolyl, isoindolyl, indolinyl, quinolinyl, dihydroquinolinyl, tetrahydroquinolinyl, isoquinolinyl, dihydroisoquinolinyl and tetrahydroisoquinolinyl, wherein said heterocyclic moieties are optionally substituted with halo, $C_{1-4}$alkyl, $C_{1-4}$alkoxy or cyano, then $R^1$ is H or $C_{1-3}$alkyl;

if $R^4$ or $R^5$ are attached to $G^1$, then $G^1$ is C;

if $A^4$, $R^4$ or $R^5$ are attached to X, then X is C;

if $A^4$, $R^4$ or $R^5$ are attached to $X^1$, then $X^1$ is C;

if $A^4$, $R^4$ or $R^5$ are attached to $X^2$, then $X^2$ is C;

if $R^4$, or $R^5$ are attached to $X^3$, then $X^3$ is C.

2. A compound according to claim 1 wherein p is 0.

3. A compound according to claim 1 wherein G is N and $G^1$ is CH.

4. A compound according to claim 1 wherein G is S and $G^1$ is CH.

5. A compound according to claim 1 wherein G is N and $G^1$ is N.

6. A compound according to claim 1 wherein G is S and $G^1$ is N.

7. A compound according to claim 1 wherein G is O and $G^1$ is N.

8. A compound according to claim 1 wherein $R^1$ is methyl and $R^2$ is methyl.

9. A compound according to claim 1 wherein $R^1$ is H and $R^2$ is $C_{3-6}$cycloalkyl wherein said $C_{3-6}$cycloalkyl is substituted with indolyl and wherein said indolyl is optionally substituted by halo or cyano.

10. A compound according to claim 1 wherein $A^1$ is a bond, $R^1$ is methyl, $A^2$ is a bond and $R^2$ is methyl.

11. A compound according to claim 1 wherein $R^3$ is H and m is 1.

12. A compound according to claim 1 wherein $R^3$ is methyl and m is 1.

13. A compound according to claim 1 wherein $R^4$ and $R^5$ are halo.

14. A compound according to claim 1 wherein $R^4$ is $C_{1-3}$alkyl and is attached to $G^1$.

15. A compound according to claim 1 wherein $R^4$ is $C_{1-3}$perfluoroalkyl and is attached to $G^1$.

16. A compound according to claim 1 wherein $R^4$ is hydrogen.

17. A compound according to claim 1 wherein $R^4$ is fluoro.

18. A compound according to claim 1 wherein $R^4$ is cyano.

19. A compound according to claim 1 wherein $R^4$ and $R^5$ are each fluoro.

20. A compound according to claim 1 wherein the hydrogen atom attached to D is in the trans configuration to the hydrogen atom attached to E.

21. A compound according to claim 1 wherein die hydrogen atom attached to D is in the cis configuration to the hydrogen atom attached to E.

22. A compound according to claim 1 wherein D in relation to the four moieties to which it is attached has an absolute configuration of S; E in relation to the four moieties to which it is attached has an absolute configuration of S.

23. A compound according to claim 1 wherein D in relation to the four moieties to which it is attached has an absolute configuration of S; E in relation to the four moieties to which it is attached has an absolute configuration of R.

24. A compound according to claim 1 wherein D in relation to the four moieties to which it is attached has an absolute configuration of R; E in relation to the four moieties to which it is attached has an absolute configuration of S.

25. A compound according to claim 1 wherein D in relation to the four moieties to which it is attached has an absolute configuration of R; E in relation to the four moieties to which it is attached has an absolute configuration of R.

26. A compound according to claim 1 wherein $A^3$ is $C_{1-4}$alkylene.

27. A compound according to claim 1 wherein $A^3$ is $C_{1-4}$alkylidene.

28. A compound according to claim 1 wherein $A^3$ is methylene.

29. A compound according to claim 1 wherein $A^3$ is a bond.

30. A compound according to claim 1 wherein $A^4$ is a bond.

31. A compound according to claim 1 wherein $A^4$ is methylene.

32. A compound according to claim 1 wherein $A^4$ is attached $X^1$.

33. A compound according to claim 1 wherein $A^4$ is attached X.

34. A compound according to claim 1 wherein $R^4$ is attached X.

35. A compound according to claim 1 wherein $R^4$ is attached $X^1$.

36. A compound according to claim 1 wherein $R^4$ is cyano or halo and n is 0.

37. A compound according to claim 1 wherein $R^1$ is independently selected from the group of heterocylic moieties consisting of thienyl, furanyl, pyrrolyl, pyrrolinyl, pyrrolidinyl, imidazolyl, imidazolinyl, imidazolidinyl, pyrazolyl, pyrazolinyl, pyrazolidinyl, pyridyl, pyrimidinyl, piperidinyl, piperazinyl, morpholino, adamantyl, indolyl, isoindolyl, indolinyl, quinolinyl, dihydroquinolinyl, tetrahydroquinolinyl, isoquinolinyl, dihydroisoquinolinyl and tetrahydroisoquinolinyl, wherein said heterocyclic moieties are optionally substituted with halo, $C_{1-4}$alkyl, $C_{1-4}$alkoxy or cyano; $A^1$ is $C_{1-4}$alkylene; $R^2$ is H or $C_{1-3}$alkylene; and $A^2$ is a bond.

38. A compound according to claim 1 wherein $R^1$ is independently selected from the group of heterocyclic moieties consisting of thienyl, imidazolyl, pyridyl, piperidinyl, piperazinyl, morpholino, adamantyl, indolyl, tetrahydroquinolinyl and tetrahydroisoquinolinyl; $A^1$ is $C_{1-4}$alkylene; $R^2$ is H or $C_{1-3}$alkylene; and $A^2$ is a bond.

39. A compound according to claim 1 wherein $R^2$ is independently selected from the group of heterocyclic moieties consisting of thienyl, furanyl, pyrrolyl, pyrrolinyl, pyrrolidinyl, imidazolyl, imidazolinyl, imidazolidinyl, pyrazolyl, pyrazolinyl, pyrazolidinyl, pyridyl, pyrimidinyl, piperidinyl, piperazinyl, morpholino, adamantyl, indolyl, isoindolyl, indolinyl, quinolinyl, dihydroquinolinyl, tetrahydroquinolinyl, isoquinolinyl, dihydroisoquinolinyl and tetrabydroisoquinolinyl, wherein said heterocylic moieties are optionally substituted with halo, $C_{1-4}$alkyl; $C_{1-4}$alkoxy or cyano; $A^2$ is $C_{1-4}$alkylene; $R^1$ is H or $C_{1-3}$alkylene; and $A^1$ is a bond.

40. A compound according to claim 1 wherein $R^2$ is independently selected from the group of heterocyclic moieties consisting of thienyl, imidazolyl, pyridyl, piperidinyl, piperazinyl, morpholino, adamantyl, indolyl, tetrahydroquinolinyl and tetrahydroisoquinolinyl; $A^2$ is $C_{1-4}$alkylene; $R^1$ is H or $C_{1-3}$alkylene; and $A^1$ is a bond.

41. A compound according to claim 1 wherein $R^1$ and $R^2$ are independently H, $C_{1-3}$alkyl, $C_{1-3}$cycloalkyl phenyl, —O-phenyl, or —N(H)C(O)O—$C_{1-4}$alkyl.

42. A compound according to claim 1 wherein $R^1$ and $R^2$ are independently H, $C_{1-3}$alkyl, or —N(H)C(O)O—$C_{1-4}$ alkyl.

43. A compound according to claim 1 wherein $R^1$ and $R^2$ are independently H, $C_{1-3}$alkyl, $C_{3-6}$cycloalkyl, phenyl, or —O-phenyl.

44. A compound according to claim 1 wherein $R^1$ and $R^2$ are independently H, $C_{1-3}$alkyl, or are independently selected from the group of heterocyclic moieties consisting of thienyl, imidazolyl, pyridyl, piperidinyl, piperazinyl, morpholino, adamantyl, indolyl, tetrahydroquinolinyl and tetrahydroisoquinolinyl.

45. A compound according to claim 1 wherein $R^2$ is H or $C_{1-3}$alkyl and $R^1$ is $C_{3-6}$cycloalkyl, phenyl, —O-phenyl, or —N(H)C(O)O—$C_{1-4}$alkyl.

46. A compound according to claim 1 wherein $R^2$ is H or $C_{1-3}$alkyl and $R^1$ is N(H)C(O)O—$C_{1-4}$alkyl.

47. A compound according to claim 1 wherein $R^2$ is H or $C_{1-3}$alkyl and $R^1$ is $C_{3-6}$cycloalkyl, phenyl or —O-phenyl.

48. A compound according to claim 1 wherein $R^2$ is H or $C_{1-3}$alkyl and $R^1$ is selected from the group of heterocylic moieties consisting of thienyl, imidazolyl, pyridyl, piperidinyl, piperazinyl, morpholino, adamantyl, indolyl, tetrahydroquinolinyl and tetrahydroisoquinolinyl.

49. A compound according to claim 1 wherein $R^1$ is H or $C_{1-3}$alkyl and $R^2$ is $C_{3-6}$cycloalkyl, phenyl, —O-phenyl, or —N(H)C(O)O—$C_{1-4}$alkyl.

50. A compound according to claim 1 wherein $R^1$ is H or $C_{1-3}$alkyl and $R^2$ is N(H)C(O)O—$C_{1-4}$alkyl.

51. A compound according to claim 1 wherein $R^1$ is H or $C_{1-3}$alkyl and $R^2$ is $C_{3-6}$cycloalkyl, phenyl or —O-phenyl.

52. A compound according to claim 1 wherein $R^1$ is H or $C_{1-3}$alkyl and $R^2$ is selected from the group of heterocyclic moieties consisting of thienyl, imidazolyl, pyridyl, piperidinyl, piperazinyl, morpholino, adamantyl, indolyl, tetrahydroquinolinyl and tetrahydroisoquinolinyl.

53. A compound according to claim 1 wherein $-A^1-R^1$ and $-A^2-R^2$ together with the nitrogen to which they are attached form pyrrolidinyl, piperidinyl, piperazinyl, morpholino, tetrahydroquinolinyl or tetrahydroisoquinolinyl and are optionally substituted with benzyl.

54. A compound according to claim 1 wherein
$A^1$ and $A^2$ are each independently $C_{1-4}$alkylene or a bond;
$A^3$ is $C_{1-4}$alkylene;
$A^4$ is bond and is attached to X or $X^1$;
X and $X^1$ are each independently C or CH;
$X^2$ and $X^3$ are each CH;
p is 0;
$R^1$ and $R^2$ are independently H, $C_{1-3}$alkyl, $C_{3-6}$cycloalkyl, phenyl, —O-phenyl. —N(H)C(O)O—$C_{1-4}$ alkyl or $C_{1-4}$alkyl-N(H)C(O)O—;
said $C_{3-6}$cycloalkyl, phenyl or O-phenyl being independently and optionally substituted with $C_{1-4}$alkyl, $C_{1-4}$alkoxy or halo;
or are independently selected from the group of heterocyclic moieties consisting of thienyl, furanyl, pyrrolyl, pyrrolinyl, pyrrolidinyl, imidazolyl, imidazolinyl, imidazolidinyl, pyrazolyl, pyrazolinyl, pyrazolidinyl, pyridyl, pyrimidinyl, piperidinyl, piperazinyl, morpholino, adamantyl, indolyl, isoindolyl, indolinyl, quinolinyl, dihydroquinolinyl, tetrahydroquinolinyl, isoquinolinyl, dihydroisoquinolinyl and tetrahydroisoquinolinyl, wherein said heterocyclic moieties are optionally substituted with halo, $C_{1-4}$alkyl, $C_{1-4}$alkoxy or cyano;
or wherein $-A^1-R^1$ and $-A^2-R^2$ together with the nitrogen to which they are attached form pyrrolidinyl, piperidinyl, piperazinyl, morpholino, dihydroquinolinyl, tetrahydroquinolinyl, dihydroisoquinolinyl or tetrahydroisoquinolinyl and are optionally substituted with halo, $C_{1-4}$alkyl, $C_{1-4}$alkoxy, cyano or benzyl;
$R^3$ is H or $C_{1-4}$alkyl;
m is 1;
$R^4$ is hydrogen, cyano, halo, nitro, $C_{1-3}$alkyl or $C_{1-3}$perfluoroalkyl and is attached to X or $X^1$;
n is 0;
G is N;
$G^1$ is CH;
Y is (D)H wherein D is C; and
Z is (E)H wherein E is C;
provided that
if $R^1$ is —N(H)C(O)O$C_{1-4}$alkyl, $C_{1-4}$alkyl-N(H)C(O)O— or said heterocyclic moiety wherein said heterocyclic moiety contains a nitrogen atom and said nitrogen acorn is attached to $A^1$, then $A^1$ is $C_{2-4}$alkylene;
if $R^2$ is —N(H)C(O)O—$C_{1-4}$alkyl, $C_{1-4}$alkyl-N(H)C(O)O— or said heterocyclic moiety wherein said heterocyclic moiety contains a nitrogen atom and said nitrogen atom is attached to $A^2$, then $A^2$ is $C_{2-4}$alkylene;

if $R^1$ is N(H)C(O)O—$C_{1-4}$alkyl, $C_{1-4}$alkyl-N(N)C(O)O— or a heterocyclic moiety selected from the group consisting of thienyl, furanyl, pyrrolyl, pyrrolinyl, pyrrolidinyl, imidazolyl, imidazolinyl, imidazolidinyl, pyrazolyl, pyrazolinyl, pyrazolidinyl, pyridyl, pyrimidinyl, piperidinyl, piperazinyl, morpholino, adamantyl, indolyl, isoindolyl, indolinyl, quinolinyl, dihydroquinolinyl, tetrahydroquinolinyl, isoquinolinyl, dihydroisoquinolinyl and tetrahydroisoquinolinyl, wherein said heterocyclic moieties are optionally substituted with halo, $C_{1-4}$alkyl, $C_{1-4}$alkoxy or cyano, then R is H or $C_{1-3}$alkyl;

if $R^2$ is —N(H)C(O)O—$C_{1-4}$alkyl, $C_{1-4}$alkyl-N(H)C(O)O— or a heterocyclic moiety selected from the group consisting of thienyl, furanyl, pyrrolyl, pyrrolinyl, pyrrolidinyl, imidazolyl, imidazolinyl, imidazolidinyl, pyrazolyl, pyrazolinyl, pyrazolidinyl, pyridyl, pyrimidinyl, piperidinyl, piperazinyl, morpholino, adamantyl, indolyl, isoindolyl, indolinyl, quinolinyl, dihydroquinolinyl, tetrahydroquinolinyl, isoquinolinyl, dihydroisoquinolinyl and tetrahydroisoquinolinyl, wherein said heterocylic moieties are optionally substituted with halo, $C_{1-4}$alkyl, $C_{1-4}$alkoxy or cyano, then $R^1$ is H or $C_{1-3}$alkyl;

if $A^4$ or are attached to X, then X is C;

if $A^4$ or $R^4$ are attached to $X^1$, then $X^1$ is C.

55. A pharmaceutically acceptable formulation comprising a compound according to claim 1.

56. A method of treating depression, attention deficit hyperactivity disorder, obsessive-compulsive disorder, and sexual dysfunction comprising the administration to a human in need thereof an effective amount of a pharmaceutically acceptable formulation comprising a compound according to claim 1.

57. A method of treating sexual dysfunction comprising the administration to a human in need thereof an effective amount of a pharmaceutically acceptable formulation comprising a compound according to claim 1.

58. A method of treating premature ejaculation comprising the administration to a human in need thereof an effective amount of a pharmaceutically acceptable formulation comprising a compound according to claim 1.

59. A compound or pharmaceutically acceptable salt or solvate thereof selected from the group consisting of
trans-3-(2-dimethylaminomethyl-cyclopentyl)-1H-indole-5-carbonitrile;
trans-3-(2-methylaminomethyl-cyclopentyl)-1H-indole-5-carbonitrile;
trans-3-(2-ethylaminomethyl-cyclopentyl)-1H-indole-5-carbonitrile;
trans-3-(2-diethylaminomethyl-cyclopentyl)-1H-indole-5-carbonitrile;
trans-3-(2[(ethyl-methyl-amino)-methyl]-cyclopentyl)-1H-indole-5-carbonitrile;
trans-3-(2-pyrrolindin-1-ylmethyl-cyclopentyl)-1H-indole-5-carbonitrile;
trans-3-{2-[(benzyl-methyl-amino)-methyl]-cyclopentyl}-1H-indole-5-carbonitrile;
trans-3-(2-dimethylaminomethyl-cyclopentyl)-1-methyl-1H-indole-5carbonitrile;
trans-3-(2-dimethylaminomethyl-cyclopentyl)-1-ethyl-1H-indole-5-carbonitrile;
trans-5-(2-dimethylaminomethyl-cyclopentyl-1H-indole-3-carbonitrile;
trans-5-(2-methylaminomethyl-cyclopentyl)-1H-indole-3-carbonitrile;
trans-5-(2-pyrrolidin-1-ylmethyl-cyclopentyl)-1H-indole-3-carbonitrile;
trans-5-(2-ethylaminomethyl-cyclopentyl)-1H-indole-3-carbonitrile;
trans-5-{2-[(ethyl-methyl-amino)-methyl]-cyclopentyl}-1H-indole-3-carbonitrile;
trans-5-(2-diethylaminomethyl-cyclopentyl)-1H-indole-3-carbonitrile;
trans-5-{2-[(benzyl-methyl-amino)-methyl]-cyclopentyl}-1-1H-indole-3-carbonitrile;
trans-5-(2-dimethylaminomethyl-cyclopentyl)-1-methyl-1H-indole-3-carbonitrile;
cis-5-(2-methylaminomethyl-cyclopentyl)-1H-indole-3-carbonitrile;
cis-5-(2-dimethylaminomethyl-cyclopentyl)-1H-indole-3-carbonitrile;
(1R,2R)-3-(2-dimethylaminomethyl-cyclopentyl)-1H-indole-5-carbonitrile;
(1S,2S)-3-(2-dimethylaminomethyl-cyclopentyl)-1H-indole-5-carbonitrile;
(+) trans-3-[2-(1-dimethylaminoethyl)cyclopentyl]-1H-indole-5-carbonitrile;
(−) trans-3-[2-(1-dimethylaminoethyl)cyclopentyl]-1H-indole-5-carbonitrile;
(+) trans-3-[2-(1-dimethylaminopropyl)cyclopentyl]-1H-indole-5-carbonitrile;
(−) trans-3-[2-(1-dimethylaminopropyl)cyclopentyl]-1H-indole-5-carbonitrile;
(1S,2S)-[2-(5-iodo-1H-indole-3-yl)-cyclopentylmethyl]-dimethylamine;
3-(2-dimethylamino-cyclopentylmethyl)-1H-indole-5-carbonitrile;
3-(2-methylamino-cyclopentylmethyl)-1H-indole-5-carbonitrile;
3-(2-ethylamino-cyclopentylmethyl)-1H-indole-5-carbonitrile;
3-(2-diethylamino-cyclopentylmethyl)-1H-indole-5-carbonitrile;
3-[2-(ethyl-methyl-amino)-cyclopentylmethyl]-1H-indole-5-carbonitrile;
3-(2-pyrrolidin-1-yl-cyclopentylmethyl)-1H-indole-5-carbonitrile; and
3-[2-(benzyl-methyl-amino)-cyclopentylmethyl]-1H-indole-5-carbonitrile.

* * * * *